United States Patent
Dumas et al.

(10) Patent No.: US 10,472,345 B2
(45) Date of Patent: Nov. 12, 2019

(54) METHODS OF PREPARING HYDROXYLAMINE DERIVATIVES USEFUL IN THE PREPARATION OF ANTI-INFECTIVE AGENTS

(71) Applicants: MERCK SHARP & DOHME CORP., Rahway, NJ (US); MERCK SHARP & DOHME LIMITED, Hoddesdon, Hertfordshire (GB)

(72) Inventors: Aaron M. Dumas, Hertford (GB); Jeremy P. Scott, Hertford (GB); Michael Shevlin, Middlesex, NJ (US); Zhijian Liu, Kendall Park, NJ (US); John Y. L. Chung, Edison, NJ (US); Feng Xu, Staten Island, NY (US); Dongfang Meng, Morganville, NJ (US)

(73) Assignees: Merck Sharp & Dohme Corp., Rahway, NJ (US); Merck Sharp & Dohme Limited, Hoddesdon, Hertfordshire (GB)

( * ) Notice: Subject to any disclaimer, the term of this patent is extended or adjusted under 35 U.S.C. 154(b) by 0 days.

(21) Appl. No.: 16/074,141

(22) PCT Filed: Jan. 30, 2017

(86) PCT No.: PCT/US2017/015541
§ 371 (c)(1),
(2) Date: Jul. 31, 2018

(87) PCT Pub. No.: WO2017/136254
PCT Pub. Date: Aug. 10, 2017

(65) Prior Publication Data
US 2019/0055216 A1  Feb. 21, 2019

Related U.S. Application Data

(60) Provisional application No. 62/290,990, filed on Feb. 4, 2016.

(51) Int. Cl.
| | | |
|---|---|---|
| C07D 211/60 | (2006.01) | |
| C07D 401/12 | (2006.01) | |
| C07D 211/78 | (2006.01) | |
| C07C 381/00 | (2006.01) | |
| C07C 249/08 | (2006.01) | |
| C07C 251/38 | (2006.01) | |

(52) U.S. Cl.
CPC .......... *C07D 401/12* (2013.01); *C07C 249/08* (2013.01); *C07C 251/38* (2013.01); *C07C 381/00* (2013.01); *C07D 211/60* (2013.01); *C07D 211/78* (2013.01)

(58) Field of Classification Search
CPC .................................................. C07D 211/60
USPC ...................................................... 546/189
See application file for complete search history.

(56) References Cited

U.S. PATENT DOCUMENTS

| | | |
|---|---|---|
| 5,349,063 A | 9/1994 | Joshua et al. |
| 6,924,327 B2 | 8/2005 | Sano et al. |
| 8,487,093 B2 | 7/2013 | Blizzard et al. |
| 9,181,250 B2 | 11/2015 | Abe et al. |
| 9,604,985 B2 | 3/2017 | Miller et al. |
| 9,708,320 B2 | 7/2017 | Abe et al. |
| 2001/0047116 A1 | 11/2001 | Matos et al. |
| 2006/0183930 A1 | 8/2006 | Dreisbach et al. |
| 2010/0130782 A1 | 5/2010 | O'Shea et al. |
| 2012/0053350 A1 | 3/2012 | Mangion et al. |
| 2013/0012712 A1 | 1/2013 | Priour et al. |
| 2015/0112070 A1 | 4/2015 | Ronsheim et al. |

FOREIGN PATENT DOCUMENTS

| | | |
|---|---|---|
| WO | 2008039420 A2 | 4/2008 |
| WO | 201400786 A1 | 12/2014 |
| WO | 2015074546 A1 | 5/2015 |

OTHER PUBLICATIONS

International Search Report and Written Opinion for PCT/US17/015541, dated Apr. 4, 2017, 17 pages.
Jack E. Baldwin, A novel entry to carbenoid species via beta-ketosulfoxonium Ylides, J. Chem. Soc. Chem. Commun., 1993, 1434-1435, 18.
Mangion, Ian K. et al., Iridium-Catalyzed X-H Insertions of Sulfoxonium Ylides, Org. Lett., 2009, 3566-3569, 11.
Mangion, Ian K., A concise synthesis of a beta-lactamase Inhibitor, Organic Letters, 2011, 5480-5483, 13(20).
Marc Dittmann et al., Native chemical ligation of hydrophobic peptides in organic solvents, Journal of Peptide Science, 2010, 558-562, 16(10).
V. Herrera et al., Homogeneous hydrogenation of imines catalyzed by rhodium and iridium complexes Kinetics and mechanism of the hydrogenation of N-(B-naphthyl methylene) aniline using [Ir(COD)(PPh3)2]PF6 as catalyst precursor, Journal of Molecular Catalysis A: Chemical, 2001, 141-149, 174.

(Continued)

*Primary Examiner* — Patricia L Morris
(74) *Attorney, Agent, or Firm* — Patricia A. Shatynski; John C. Todaro

(57) ABSTRACT

The present invention relates to processes for the preparation of N-protected 4-((2S,5R)-5-((benzyloxy)amino)piperidine-2-carboxamido)piperidine-1-carboxylates. Such compounds have application in the preparation of beta-lactamase inhibitors such as 7-oxo-1,6-diazabicyclo[3.2.1]octane-2-carboxamides and esters, in particular, the beta lactamase inhibitor, (2S,5R)-7-oxo-N-piperidin-4-yl-6-(sulfoxy)-1,6-diazabicyclo[3.2.1]octane-2-carboxamide. The present invention also encompasses intermediates useful in the disclosed processes and methods for their preparation.

29 Claims, No Drawings

(56) References Cited

OTHER PUBLICATIONS

Wang, et al., One-carbon chain extension of esters to alpha-chloroketones: A safer route without diazomethane, Journal of Organic Chemistry, 2004, 1629-1633, 69.
Zhijian Liu et al., N-Boc Deprotection and Isolation method for Water-Soluble Zwitterionic Compounds, The Journal of Organic Chemistry, 2014, 11792-11796, 79(23).
Supplemental European Search Report for EP 177479656 dated Sep. 17, 2019, 7 pages.

METHODS OF PREPARING HYDROXYLAMINE DERIVATIVES USEFUL IN THE PREPARATION OF ANTI-INFECTIVE AGENTS

CROSS REFERENCE TO RELATED APPLICATIONS

This application is a U.S. National Phase application under 35 U.S.C. § 371 of PCT Application No. PCT/US2017/015541, filed Jan. 30, 2018 which claims priority under 35 U.S.C. § 119(e) from U.S. Provisional Application Ser. No. 62/290,990, filed on Feb. 4, 2016.

FIELD OF THE INVENTION

The present invention relates to processes for the preparation of N-protected 4-((2S,5R)-5-((benzyloxy)amino)piperidine-2-carboxamido)piperidine-1-carboxylates. Such compounds have application in the preparation of beta-lactamase inhibitors such as 7-oxo-1,6-diazabicyclo[3.2.1]octane-2-carboxamides and esters, in particular, the beta lactamase inhibitor, (2S,5R)-7-oxo-N-piperidin-4-yl-6-(sulfoxy)-1,6-diazabicyclo[3.2.1]octane-2-carboxamide. The present invention also encompasses intermediates useful in the disclosed processes and methods for their preparation.

BACKGROUND OF THE INVENTION

Certain 7-oxo-1,6-diazabicyclo[3.2.1]octane-2-carboxamides are inhibitors of 3-lactamase and, when used in conjunction with β-lactam antibiotics, can be effective for the treatment of bacterial infections, e.g., by overcoming resistance mechanisms. See, for example, International Patent Application Publication No. WO2009/091856 which discloses 7-oxo-1,6-diazabicyclo[3.2.1]octane-2-carboxamides and their synthesis from a ketosulfoxonium ylide intermediate containing an amide side chain, where the ylide intermediate is cyclized to a 5-oxo-piperidine-2-carboxamide using an Ir, Rh, or Ru catalyst. Similarly, Baldwin et al. disclose the transformation of lactone-derived β-ketosulfoxonium ylides into β-oxonitrogen heterocycles in the presence of a rhodium catalyst. See Baldwin et al., 1993, *J. Chem. Soc., Chem. Commun.* 18:1434-1435. Mangion et al. disclose iridium-catalyzed X—H insertions (e.g., N—H insertions) of sulfoxonium ylides. See Mangion et al., 2009, *Org. Lett.*, 11:3566-3569 and Mangion et al., 2011, *Org. Lett.* 13:5480-5483.

U.S. Patent Application Publication No. US2003/0199541 discloses methods for preparing azabicyclic compounds which are useful as medicaments, in particular anti-bacterial agents. International Patent Application Publication No. WO2008/039420 discloses methods for preparing certain 7-oxo-2,6-diazabicyclo[3.2.0]heptane-2-carboxamides which are useful as β-lactamase inhibitors.

U.S. Pat. No. 6,924,327 and Wang et al., 2004, *J. Org. Chem.* 69:1629 describe the use of trimethylsulfoxonium iodide to prepare chloroketones. International Patent Application Publication No. WO2010/126820 discloses the preparation of alkyl esters of N-protected oxo-azacycloalkylcarboxylic acids. These esters can be used as intermediates in the synthesis of 7-oxo-1,6-diazabicyclo[3.2.1]octane-2-carboxamides and esters. International Patent Application Publication No. WO2014/200786 discloses the preparation of N-protected 6-(piperidin-4-ylcarbamoyl)piperidin-3-yl sulfonates. These sulfonates are suitable for use as intermediates that lead via a series of additional process steps to the synthesis of 7-oxo-1,6-diazabicyclo[3.2.1]octane-2-carboxamides and esters. U.S. Patent Application Publication No. 2015/0141401 describes processes and intermediates useful for the synthesis of beta-lactamase inhibitors.

SUMMARY OF THE INVENTION

The present invention relates to chemical processes and intermediates useful in the synthesis of the compound of Formula I, and related compounds, that are useful as intermediates in the preparation of compounds that are potent inhibitors of beta-lactamase.

The chemical processes of the present invention afford advantages over previously known procedures and include a more efficient, high-yielding and cost-effective route to the compound of Formula I and salts thereof. Specifically, the chemical processes of the present invention offer efficient synthetic routes compared to the previously reported processes.

In addition, the chemical processes of this invention are believed to afford operational advantages on an industrial scale.

Accordingly, the present invention provides a process for preparing a compound of Formula I:

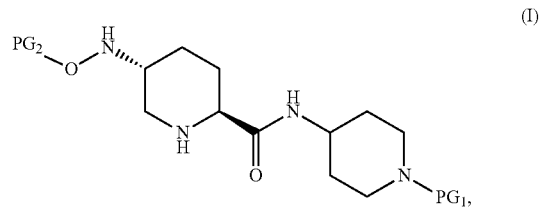

(I)

or a salt thereof,
which comprises a reduce/couple sequence or a couple/reduce sequence,
wherein
the reduce/couple sequence comprises
(E1) reducing a compound of Formula V:

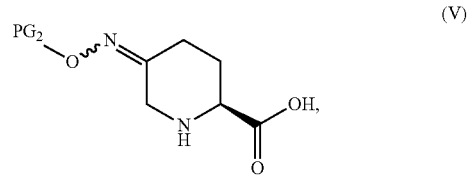

(V)

or an acidic or basic salt thereof,
to obtain a compound of Formula VI;

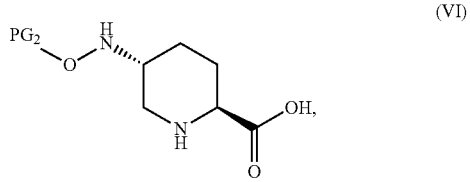

(VI)

or an acidic or basic salt thereof; and
(F1) coupling the compound of Formula VI, or an acidic or basic salt thereof, with a compound of formula VII,

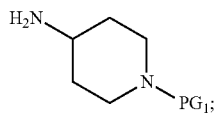

or a salt thereof,
to form the compound of Formula I;
the couple/reduce sequence comprises
(E2) coupling a compound of Formula V:

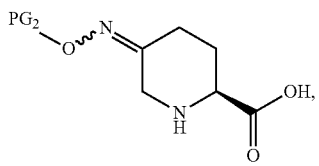

or an acidic or basic salt thereof,
with a compound of Formula VII,

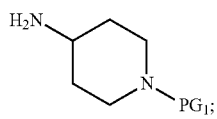

or a salt thereof,
to obtain a compound of Formula VIII

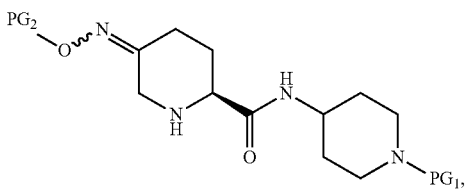

or a salt thereof; and
(F2) reducing the compound of Formula VIII, or a salt thereof, to form the compound of Formula I.

In select embodiments, each instance of $PG_1$ is independently an amine protecting group which forms with the amino nitrogen to which it is attached a carbamate, a benzylamine, or a sulfonamide; and $PG_2$ is an oxygen protecting group (also referred to as an alcohol protecting group) selected from acetyl (Ac), benzyl (Bn), 4-MeOBn, benzoyl (Bz), and tert-Butyldimethylsilyl ether (TBS).

Compounds of Formula I are useful as intermediates that in combination with a series of additional steps results in a convergent synthesis of 7-oxo-1,6-diazabicyclo[3.2.1]octane-2-carboxamides and 2-carboxylic esters that can be used as β-lactamase inhibitors (BLIs).

Other embodiments, aspects and features of the present invention are either further described in or will be apparent from the ensuing description, examples, and appended claims.

DETAILED DESCRIPTION OF THE INVENTION

The present invention (alternatively referred to herein as "Process P") includes processes for preparing a compound of Formula I, and salts thereof, which comprises steps E1 (reduce) and F1 (couple), or, alternatively, steps E2 (couple) and F2 (reduce), as set forth above in the Summary of the Invention. These compounds and their salts are useful as intermediates for the preparation of beta-lactam antibiotics.

Definitions

The amine protective group $PG_1$, as used in the reactions described herein, in combination with the amino nitrogen to which it is attached, can be a carbamate or a benzylamine or a sulfonamide. Suitable carbamate, benzylamine and sulfonamide protective groups and methods for their formation and cleavage are described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. In one embodiment, $PG_1$ is (1) —C(=O)—O—(CH$_2$)$_{0-1}$—CH=CH$_2$, (2) —C(=O)—O—CH$_2$-AryB, wherein AryB is phenyl which is optionally substituted with from 1 to 3 substituents each of which is independently halo, —NO$_2$, —C$_{1-4}$ alkyl, or —O—C$_{1-4}$ alkyl, (3) —C(=O)—O—C$_{1-4}$ alkyl, or (4) —CH$_2$-AryC in which AryC is phenyl which is optionally substituted with from 1 to 3 substituents each of which is independently halo, —NO$_2$, —C$_{1-4}$ alkyl, or —O—C$_{1-4}$ alkyl. In another embodiment, $PG_1$ is t-butyloxycarbonyl (Boc), allyloxycarbonyl (Alloc), benzyloxycarbonyl (Cbz), p-methoxybenzyloxycarbonyl, p-nitrobenzyloxycarbonyl, p-bromobenzyloxycarbonyl, p-chlorobenzyloxycarbonyl, 2,4-dichlorobenzyloxycarbonyl, or benzyl. In still another embodiment, $PG_1$ is Boc. In still another embodiment, $PG_1$ is a sulfonyl group generated from sulfonyl halides such as methanesulfonyl chloride, chloromethanesulfonyl chloride, dichloromethanesulfonyl chloride, benzenesufonyl chloride, p-trifluoromethylbenzenesulfonyl chloride, p-toluenesulfonyl chloride, p-bromobenzenesulfonyl chloride, p-fluorobenzenesulfonyl chloride, p-methoxybenzenesulfonyl chloride, 2-nitrobenzenesulfonyl chloride, 4-nitrobenzenesulfonyl chloride, 2,4-dichlorobenzenesulfonyl chloride, chloromethanesulfonyl chloride, p-trifluoromethylbenzenesulfonyl chloride, p-bromobenzenesulfonyl chloride, 2,4-dichlorobenzenesulfonyl chloride, chloromethanesulfonyl chloride, p-trifluoromethylbenzenesulfonyl chloride and p-bromobenzenesulfonyl chloride. $PG_1$ is stable under conditions which the $PG_2$ group comes off.

$PG_2$ is an oxygen protective group. $PG_2$, in combination with the oxygen to which it is attached, is suitably acetyl, benzyl, benzoyl, β-methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl] (MMT), p-methoxybenzyl ether (PMB or 4-MeOBn), methylthiomethyl ether, pivaloyl (Piv), tetrahydropyranyl (THP), tetrahydrofuran (THF), trityl (triphenylmethyl, Tr), Silyl ether (including trimethylsilyl (TMS), tert-butyldimethylsilyl (TBDMS or TBS), triisopropylsilyloxymethyl (TOM), and triisopropylsilyl (TIPS) ethers), methyl ethers and ethoxyethyl ethers (EE). In one embodiment, $PG_2$ is benzyl.

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl and pentyl alkyl isomers as well as n-, iso, sec- and t-butyl, n- and iso-propyl, ethyl and methyl. As another example, "$C_{1-4}$ alkyl" refers to any of n-, iso-, sec- and t-butyl, n- and isopropyl, ethyl and methyl. As another example, "$C_{1-3}$ alkyl" refers to any of n-propyl, isopropyl, ethyl and methyl.

The term "halogen" or "halo" means fluorine (F), chlorine (Cl), bromine (Br), and iodine (I). In specific embodiments, "halo" means chlorine or bromine. Similarly, "halo" means any of fluoro, chloro, bromo, and iodo groups. In specific embodiments, "halo" means chloro or bromo.

Unless expressly stated to the contrary, all ranges cited herein are inclusive. For example, a cycloalkyl ring described as a "$C_{3-8}$cycloalkyl" means the ring can contain 3, 4, 5, 6, 7 or 8 atoms in the ring. It is also to be understood that any range cited herein includes within its scope all of the sub-ranges as distinct embodiments within that range.

In addition, the term "or," as used herein, denotes alternatives that may, where appropriate, be combined; that is, the term "or" includes each listed alternative separately as well as their combination.

Unless expressly stated to the contrary, substitution by a named substituent is permitted on any atom provided such substitution is chemically allowed and results in a stable compound. A "stable" compound is a compound that can be prepared and isolated and whose structure and properties remain or can be caused to remain essentially unchanged for a period of time sufficient to allow use of the compound for the purposes described.

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

The compounds prepared via the present invention may be chiral as a result of asymmetric centers, chiral axes, or chiral planes as described in: E. L. Eliel and S. H. Wilen, *Stereochemistry of Carbon Compounds*, John Wiley & Sons, New York, 1994, pages 1119-1190), and may occur as single optical isomers or as mixtures of any number of the possible optical isomers, including racemates, racemic mixtures, diastereomers, diastereomeric mixtures, enantiomers, and enantiomeric mixtures. In certain instances, the compounds disclosed may exist as tautomers and all tautomeric forms are intended to be encompassed by the scope of the invention, even though only one tautomeric structure is depicted. That is, for the purposes of the present invention, a reference to a compound of Formula I is a reference to the compound per se, or to any one of its tautomers per se, or to mixtures of two or more tautomers.

Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The compounds of the present invention may be in the form of salts, and reference to compounds and to structures includes reference to salts of the compounds or structures. Salts may be prepared from bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from organic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethyl aminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic and trifluoroacetic acids and the like. Particularly preferred are citric, fumaric, hydrobromic, hydrochloric, maleic, phosphoric, sulfuric, and tartaric acids.

Processes of the Invention

Steps E1 and F1 involve, in certain embodiments, the reduction of a compound of Formula V to form a compound of Formula VI, followed by coupling of the compound of Formula VI with a compound of Formula VII to form a compound of Formula I.

In certain embodiments, the highly diastereoselective reduction of a compound of Formula V to a compound of Formula VI in step E1 involving, e.g., a protic acid, a transition metal catalyst and hydrogen gas, proceeds in >95:5 diastereomeric ratio (d.r.) favoring the desired trans diastereomer and with minimal overreduction. In certain embodiments, the highly diastereoselective reduction of a compound of Formula V to a compound of Formula VI in step E1 involving, e.g., a iron(III) promoted borohydride reduction (in the absence of hydrogen gas), proceeds in ~95:5 diastereomeric ratio (d.r.) favoring the desired trans diastereomer and with minimal overreduction. Previous methods to accomplish related reductions (on esters of compounds of Formula V) generally gave lower selectivity (~80:20 d.r.) using protic acids and hydride sources. Additionally, most existing transition metal-catalyzed oxime reductions lead to overreduction and formation of the corresponding amines rather than the desired hydroxylamine derivatives.

Steps E2 and F2 provide an alternative means to obtain a compound of Formula I from the compound of Formula V by reversing the order of the reduction and coupling steps in E1 and F1. Steps E2 and F2, in certain embodiments, involve the coupling of a compound of Formula V with a compound of Formula VII to form a compound of Formula VIII, followed by reduction of the compound of Formula VIII to form a compound of Formula I.

The starting material of Formula V or Formula VIII contain a NO-$PG_2$ and can be in the form of a protonated ammonium salt or deprotonated carboxylate.

The reduction reaction in steps E1 and F2 are conducted with an appropriate ligand in the presence of a transition metal or a borohydride reagent with or without additives described herein. The transition metal can be any metal salt, for example a cationic metal salt, including Rh(I), Ru, Pd, Ni, Cu, Fe, Co, etc. The transition metal is typically present at 0.1 mol % to 5.0 mol % or 0.001 to 0.05 equivalents. In one embodiment, the transition metal is Rh(I) for example as present in bis(norbornadiene)rhodium(I) tetrafluoroborate. The ligand can be any mono or bidentate phosphine, including, but not limited to, dcpf (1,1'-bis(dicyclohexylphosphino)ferrocene), dppo (1,8-bis(diphenylphosphino)octane), dippf (1,1'-bis(diisopropylphosphino)ferrocene), dcpp (1,3-bis(dicyclohexylphosphino)propane), dcpb (1,4-bis(dicyclohexylphosphino)butane), dpbp (2,2'-bis(diphenylphosphino) benzophenone), $PPh_3$ (triphenylphosphine), $PCy_3$ (tricyclohexylphosphine), dppf (1,1'-Bis(diphenylphosphino)ferrocene), etc. The ligand is typically present at 0.1 mol % to 10.0 mol % or 0.001 to 0.05 equivalents. In one embodiment, the ligand is bis(dicyclohexylphosphino)-ferrocene. When a transition metal is used, the reaction is performed in the presence of hydrogen gas under the pressures described herein.

Suitable borohydride reagents include anion $BH_4^-$, and its salts, and compounds containing $BH_{4-n}X_n^-$, where n is 1, 2, or 3, for example cyanoborohydride ($B(CN)H_3^-$) and triethylborohydride ($B(C_2H_5)_3H^-$). A preferred borohydride is $NaBH_4$. These borohydride reagents can be used with or without modification with 1-3 equivalents of acid, e.g., a carboxylic acid such as formic, acetic, propionic, chloroacetic, trifluoroacetic, pivalic, tartaric, malonic, etc. Additives that can used with a borohydride reagent include any acid such as HCl, $H_2SO_4$, $HBF_4$, HOTf, MsOH, TsOH or TFA, including Lewis acids such as $BF_3$ and $Me_3SiOTf$, Fe(III) salts such as $Fe(NO_3)_3$, $Fe_2(SO_4)_3$, $Fe(OAc)_3$, $Fe(OR)_3$/HCl (where $R=C_1-C_8$), particularly, $Fe(OEt)_3$/HCl and $Fe(OMe)_3$/HCl, and Fe(III) halides such as $FeCl_3$, $FeBr_3$, $FeI_3$. The borohydride reagent is typically present at 1-10 equivalents. Such an additive is typically present at 0.1-10 equivalents. In one embodiment, the additive is $NaBH_4$—$FeCl_3$ with 1-2 equiv charge of $FeCl_3$ or its hydrate.

The reduction steps E1 and F2 are conducted in any suitable solvent, including any combination of suitable solvents. Suitable solvents for the reduction steps E1 and F2 include, but are not limited to, water, methanol, ethanol, 2-propanol, 1-propanol, n-butanol, 2-butanol, isobutanol, $CF_3CH_2OH$, THF, acetone, triglyme, diglyme, 1,2-dimethoxyethane, EtOAc, MeOAc, i-PrOAc, DMF, DMAC, DMSO and MeCN. In certain embodiments, the solvent is ethanol, optionally with water, or a mixture of ethanol and triglyme, optionally with water. In certain embodiments, the solvent is a mixture of isopropyl alcohol and water. The amount of the water required for reduction could also be introduced by using hydrate salt of Fe(III) halides or Fe(III) salts.

The reduction reaction in Steps E1 and F2 can suitably be conducted at a temperature in a range of from about −70° C. to about 100° C., for example, over the course of 1 to 24 hours, and is typically conducted at a temperature in a range of from about −40° C. to about 60° C., for example, over the course of 8 hours to 24 hours. In one exemplary embodiment for hydrogenation, the reduction step is conducted at a temperature of 55° C., for example, for 18-22 hours. The hydrogen pressure is typically maintained in a range for 10-500 psi. In certain embodiments, the hydrogen pressure is in a range from about 100 to 500 psi. In one exemplary embodiment for borohydride, the reduction with a borohydride reagent is conducted at a temperature of −40 to −25° C. but may be performed at a temperature as low as −78° C.

Suitable acids for use with a transition metal in Steps E1 and F2 include any acid containing a non-coordinating counterion, including, but not limited to, $HBF_4$, $HPF_6$, $HSbF_6$, HOTf, MsOH, TsOH and TFA, and Lewis acids including, but not limited to, $BF_3$ and $Me_3SiOTf$. In one embodiment, the acid is $HBF_4$. The acid is typically employed in an amount in a range of from about 1 to about 10 equivalents per equivalent of the compound of Formula V (E1) or the compound of Formula VIII (F2), and is more typically employed in an amount in a range of from about 1 to about 2 equivalents.

Suitable acids for use with a borohydride reagent in Steps E1 and F2 include acids such as HCl, $H_2SO_4$, $HBF_4$, HOTf, MsOH, TsOH or TFA, including Lewis acids such as $BF_3$ or $Me_3SiOTf$, and Fe(III) salts such as $Fe(NO_3)_3$, $Fe_2(SO_4)_3$, Fe $(OAc)_3$, $Fe(OR)_3$/HCl (where $R=C_1-C_8$), particularly, $Fe(OEt)_3$/HCl and $Fe(OMe)_3$/HCl, and Fe(III) halides such as $FeCl_3$, $FeBr_3$, $FeI_3$. Suitable additives for use with a borohydride reagent in Steps E1 and F2 include, but are not limited to, water, and amino acids including glycine, lysine, serine, threonine, aspartic acid, tryptophan, valine, phenylalanine, glutamic acid, histidine, methionine, cysteine.

The final product of the compound of Formula VI can be either in neutral form (as drawn, which can be also be referred to as zwitterion form) or a protonated ammonium salt or a deprotonated carboxylate salt. For a protonated salt, the counterion could be $HSO_4$, $BF_4$, OTf, OMs, Cl, I, Br, $O_2CCF_3$, or OTs. Alternatively, the carboxylic acid could be deprotonated to give inorganic salts (Na, K, Li, Cs, Ca) or organic salts (morpholine, $tBuNH_2$, $Cy_2NH$, $Bn_2NH$, TRIS, cyclohexylamine, $iPr_2NH$, etc). The final product of the compound of Formula I obtained through Step F2 cannot be isolated as a carboxylate salt, only as an ammonium salt or its free base.

The coupling of hydroxylamine of Formula VI and the primary amine of Formula VII in step F1 occurs free of a protecting group on the secondary amine in the compound of Formula VI. Under the desired conditions, the carboxylic acid group in the compound of Formula VI can be activated with minimal homo-coupling to the nucleophilic secondary amine or hydroxylamine nitrogens, so that the main product, a diamine of Formula I, is selectively obtained from reaction with primary amine of Formula VII. Existing methods rely on protection of the secondary amine in the compound of Formula VI before coupling to amides.

The starting material of Formula VI contains a $NO-PG_2$ and can be introduced as neutral form (as drawn) or as any salt. The compounds of Formula VI and VII can be introduced in a neutral form or as any ammonium salt thereof including, HCl, TFA, TsOH, MsOH, $H_2SO_4$, HBr, etc. The compound of Formula VII can also contain any common PG on secondary amine instead of Boc such as CBz, Fmoc, Moc, Bn, Ac, Bz, allyl, PMB etc. In one embodiment, the compound of Formula VI is a $H_2SO_4$ salt and the compound of Formula VII is a neutral form.

The coupling reaction in steps E2 and F1 is conducted with a coupling reagent. The coupling reagent can be any carboxylic acid dehydrating agent, including carbodiimide reagents (i.e., R'—N=C=N—R" where R', R"=alkyl, cycloalkyl, or aryl) such as 1-Ethyl-3-(3-dimethylaminopropyl)carbodiimide HCl (EDC.HCl), N,N'-Dicyclohexylcarbodiimide (DCC), and N,N-Diisopropylcarbodiimide (DIC), acyl chlorides (from reaction with thionyl chloride) such as $POCl_3$, and mixed anhydrides. Representative coupling agents include 1-Ethyl-3-(3-dimethylaminopropyl)carbodiimide HCl (EDC.HCl), N,N'-Dicyclohexylcarbodiimide (DCC), N,N-Diisopropylcarbodiimide (DIC), $POCl_3$, 1-Cyano-2-ethoxy-2-oxoethylidenaminooxy)dimethylamino-morpholino-carbenium hexafluorophosphate (COMU® (Sigma-Aldrich)), 2-(1H-benzotriazol-1-yl)-1,1, 3,3-tetramethyluronium hexafluorophosphate (HBTU), O-(6-Chloro-1-hydrocibenzotriazol-1-yl)-1,1,3,3-tetramethyluronium tetrafluoroborate (TCTU), 1-[Bis(dimethylamino)methylene]-1H-1,2,3-triazolo[4,5-b]pyridinium 3-oxidhexafluorophosphate (HATU), 1,1'-Carbonyldiimidazole (CDI), (Benzotriazol-1-yloxy)tris(dimethylamino)phosphonium hexafluorophosphate (BOP), benzotriazol-1-yl-oxytripyrrolidinophosphonium hexafluorophosphate (PyBOP®), etc. Coupling reagents are described in El-Faham et al., 2011, *Chem. Rev.* 111:6557-6602. The coupling reagent is typically present at 1-5 equivalents. In one embodiment, the coupling reagent is EDC.HCl.

A peptide coupling additive is optionally added to the coupling reaction. The coupling reagent can be any peptide coupling additive, including 2-pyridinol-1-oxide (HOPO), hydroxybenzotriazole (HOBt), 3-hydroxy-1,2,3-benzotriazin-4-one (HOOBt), N-hydroxysuccinimide, Ethyl (hydroxyimino)cyanoacetate (Oxyma-Pure®), 4-Dimethylaminopyridine (DMAP), etc. See El-Faham et al., 2011, *Chem. Rev.* 111:6557-6602. If included in the coupling reaction, the peptide coupling additive is present at 0.1-5 equivalents. In one embodiment, the peptide coupling additive is HOPO.

The coupling steps E2 and F1 are conducted in any non-nucleophilic solvent system comprising one or more non-nucleophilic solvents. Suitable solvents include DMF, acetonitrile, dichloromethane, THF, 2-MeTHF, EtOAc, IPAc, DMAc, toluene, NMP, DMPU, etc. In one embodiment, the solvent system is a mixture of NMP and toluene.

The coupling reaction in Steps E2 and F1 can suitably be conducted at a temperature in a range of from about −20° C. to about 50° C., for example, over the course of 1 to 48 hours and is typically conducted at a temperature in a range of from about −5° C. to about 30° C., for example, over the course of 1 hour to 5 hours. In one exemplary embodiment, the coupling step is conducted at a temperature of 25° C., for example, for 2 hours. In another exemplary embodiment, the coupling step is conducted at a temperature of 0° C. for about 1.5 days.

Suitable acids, which are optional, in Steps E2 and F1 include any non-carboxylic acid proton source, including, but not limited to HCl, MsOH, TFA, TsOH, H$_3$PO$_4$, H$_2$SO$_4$, TfOH, CF$_3$CO$_2$H, etc. In one embodiment, the acid is HCl. If an acid is present, the acid is typically employed in an amount in a range of from about 1 to about 5 equivalents per equivalent of the compound of Formula V (E1) or the compound of Formula VIII, and is more typically employed in an amount in a range of from about 1 to about 2 equivalents.

Suitable salt additives can be used to improve the reaction rate, selectivity, yield, and physical behavior by enhancing the solubility of substrate and reagents in the reaction mixture, in particular if a protonated ammonium salt of Formula VI or V is used. Suitable salt additives in Steps E2 and F1 include, but are not limited to, carboxylate salts, quaternary ammonium phase transfer reagents, tertiary amine salts, etc. In one embodiment, the salt additive is a trifluoroacetate salt. In one embodiment, the salt additive is sodium trifluoroacetate.

Suitable base additives can be used to improve the reaction rate, selectivity, yield, and impurity profile, in particular if a protonated ammonium salt of Formula VI or V is used. Suitable base additives in Steps E2 and F1 include, but are not limited to, lutidine, collidine, pyridine, N,N-dimethylaniline, imidazole, N-methylimidazole, N-methylmorpholine, picoline, etc. In one embodiment, the base additive is 2,6-lutidine.

The final product of the coupling reaction can contain any variation of protecting groups as are found in the starting materials of the compounds of Formula VI and VII. The products can be isolated as the free base, or an ammonium salt protonated on nitrogen, with a counterion being any common salt such Cl, Br, OAc, TFA, OMs, OTs, oxalate, etc.

The compound of Formula V can be prepared from, for example, the compound of Formula III through multiple means including but not limited to those described below.

In certain embodiments of the invention, a compound of Formula V is prepared from a compound of Formula III through a cyclize/deprotection sequence or a deprotection/cyclize sequence.

In one aspect of these embodiments, the process of the invention further comprises preparing a compound of Formula V

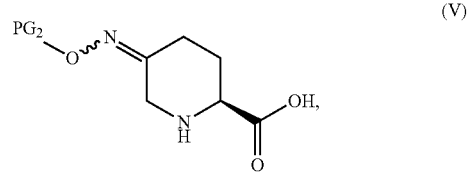

or an acidic or basic salt thereof, by
(C1) cyclizing a haloxoxime of Formula III:

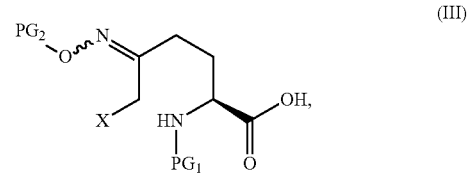

or an acidic or basic salt thereof,
wherein X is chloro, bromo or iodo,
by addition of a base to obtain a compound of Formula IV

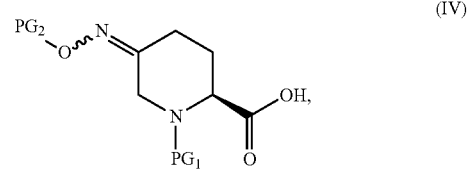

or an acidic or basic salt thereof; and
(D1) deprotecting the compound of Formula IV, or an acidic or basic salt thereof, to form a compound of Formula V, or an acidic or basic salt thereof.

The cyclization of a N-protected halooxime carboxylic acid of formula III to give the N-protected piperidine oximes of Formula IV prevents epimerization of the amino acid center so that, in certain embodiments, a compound of formula IV is formed in >99% enantiomeric ratio (e.r.). This reaction also avoids unstable halo-amine intermediates and leads to cleaner reaction profiles and higher yields than the deboc/cyclize alternative.

In the compounds of Formula III and IV, the protecting groups are orthogonal.

The cyclization reaction in step C1 is conducted with suitable base. The base can be selected from bases including, but not limited to, KOtBu, NaOtBu, LiOtBu, potassium t-pentoxide, sodium t-pentoxide, lithium t-pentoxide, $Cs_2CO_3$, LDA, LiHMDS, NaHMDS, KHMDS, DBU, DBN, NaOH, LiOH, and KOH. The base is typically present at 1-5 equivalents. In one embodiment, the base is KOtBu.

The cyclization step C1 is conducted in any solvent or combination of solvents in which the compound of Formula III or a salt thereof is at least partially soluble. Suitable solvents include, but are not limited to, THF, 2-MeTHF, acetonitrile, DMF, DMAc, NMP, toluene, dichloromethane, EtOAc, IPAc, 2-PrOH, MeOH, EtOH, and water. In one exemplary embodiment, a combination of DMF, THF and toluene is used.

The cyclization reaction in Steps C1 can suitably be conducted at a temperature in a range of from about −50° C. to about 50° C. and is typically conducted at a temperature in a range of from about −5° C. to about 30° C. The cyclization reaction is typically complete within minutes. In one exemplary embodiment, the cyclization step is conducted at a temperature of 0-5° C.

The final product of the cyclization reaction can be a free acid (as shown), inorganic salt (Li, Na, K, Ca, etc.) or organic salt (morpholine, $tBuNH_2$, $Cy_2NH$, $Bn_2NH$, TRIS, cyclohexylamine, $iPr_2NH$, etc.)

In the compounds of Formula IV, the protecting groups are orthogonal.

The deprotection step in Step D1 is conducted with any protic acid capable of removing a protecting group. Suitable protic acids include, but are not limited to, TFA, MsOH, TsOH, $HBF_4$, HCl, and TfOH. Deprotection can also be carried out with a Lewis acid such as $BF_3$, $Me_3SiX$ (where X=OTf, Cl, Br, or I) or $Me_3SiX$/BSA. In the case that Lewis acids are used, the deportection can be carried out in the absence or presence of amine bases including, but not limit to, N.N-dimethyl aniline, $Et_3N$, $i$-$Pr_2NEt$, morpholine, imidazole, pyridine, lutidine, and collidine. Deprotection can also be carried out with a strong nucleophilic base such as M-OH (where M=Li, Na, K, or Cs) or M-OMe (where M=Li, Na, K). The acid is typically employed at 1-5 equivalents for most acids, but can be used up to 20-40 equivalents (for example, TFA used as solvent or co-solvent). In one embodiment, deprotection is typically carried out with 1-5 equiv of TMSBr or TMSI in the presence or absence of BSA. In another embodiment, deprotection is typically carried out with or 0.1-2 equiv of TMSI in the presence of BSA.

The deprotection step D1 is conducted in any solvent that is relatively inert to strong acid and promotes deprotection, including, but not limited to dichloromethane, acetonitrile, 2-MeTHF, EtOAc, IPAc, toluene, and mixtures thereof.

The deprotection reaction in Step D1 can suitably be conducted at a temperature in a range of from about −50° C. to about 100° C. over the course of 10 minutes to 4 hours and is typically conducted at a temperature in a range of from about −10° C. to about 60° C., for example, over the course of 30 minutes to 1 hour. In one exemplary embodiment, the deprotection step is carried out at a temperature of 50° C., for example, over 35 min. In another exemplary embodiment, the deprotection step is carried out at a temperature of 0-5° C. overnight.

The final product of the deprotection reaction can be in a neutral form (as drawn, which can also be referred to zwitterion form) or either a protonated ammonium salt, or a deprotonated carboxylate salt. For a protonated salt, a counterion could be a conjugate base of any of the acids listed above. Alternatively, the carboxylic acid could be deprotonated to give inorganic salts (e.g., Na, K, Li, Cs, Ca) or organic salts (e.g., morpholine, $tBuNH_2$, $Cy_2NH$, $Bn_2NH$, cyclohexylamine, $iPr_2NH$, or TRIS).

In another aspect of this embodiment, the process of the invention further comprises preparing a compound of Formula V

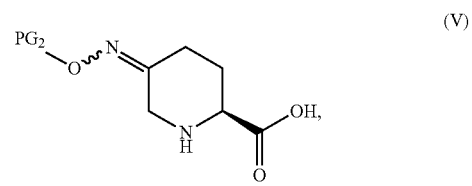

or an acidic or basic salt thereof,
by
(C2) deprotecting a compound of Formula III:

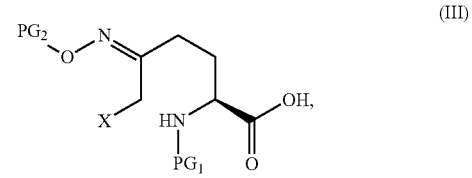

or an acidic or basic salt thereof,
wherein X is chloro, bromo or iodo, to obtain a compound of Formula IX

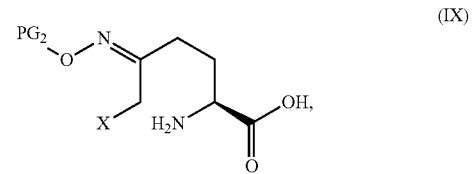

or an acidic or basic salt thereof; and
(D2) cyclizing the compound of Formula IX, or an acidic or basic salt thereof, to form a compound of Formula V, or an acidic or basic salt thereof.

The compounds of Formula III can be a free acid, or an organic salt with an ammonium counterion derived from, for example: $Et_3N$, $Cy_2NH$, Tris, morpholine, $tBuNH_2$, etc., or an inorganic salt of, for example, Li, Na, K, Ca, etc. The protecting group on nitrogen could be anything orthogonal to the protecting group on N—O-$PG_2$.

The deprotection step in Step C2 is conducted with any acid strong enough to remove a protecting group. Suitable acids include, but are not limited to, TsOH, MsOH, $HBF_4$, HCl, TFA, and $H_2SO_4$. Deprotection can also be carried out with a Lewis acid such as $BF_3$, $Me_3SiX$ (where X=OTf, Cl, Br, or I) or $Me_3SiX$/BSA. The acid is typically employed at 1-10 equivalents.

The deprotection step C2 is conducted in any non-nucleophilic solvent or mixture of solvents compatible with the acid used for deprotection step. For example, THF, 2-MeTHF, $CH_3CN$, $CH_2Cl_2$, toluene, DMF, DMAc, EtOAc, and IPAc can be used, optionally in combination with water.

The deprotection reaction in Step C2 can suitably be conducted at a temperature in a range of from about −20° C. to about 100° C., for example, over the course of 10 minutes to 4 hours and is typically conducted at a temperature in a range of from about −10° C. to about 40° C., for example, over the course of 30 minutes to 3 hours. In one exemplary embodiment, the deprotection is conducted at 25° C., for example, for 2.5 hr.

The intermediate IX formed after the deprotection reaction step will be protonated as the ammonium salt with the counterion being the conjugate base of the acid used in the deprotection step.

The cyclization reaction in step D2 is conducted with a suitable base. Any inorganic or organic base capable of inducing the cyclization of the compound of formula IX to the compound of formula V can be used. Examples of inorganic bases include, but are not limited to, $K_2CO_3$, $K_3PO_4$, $NaHCO_3$, $Na_2CO_3$, NaOH, KOH, and LiOH (added either as solids or as aqueous solutions). Examples of organic bases include, but are not limited to, $Et_3N$, $tBuNH_2$, $Cy_2NH$, TRIS, morpholine, Hunig's base, DBU, pyridine, etc. The base is typically present at 1-11 equivalents. If using a dibasic or tribasic base, 1 equivalent more than the amount of acid added would typically be needed. In one embodiment, the base is NaOH.

If the cyclization step D2 is conducted in the solvent used in step C2, water could be used in the cyclize step as a co-solvent.

The cyclization reaction in Steps D2 can suitably be conducted at a temperature in a range of from about −50° C. to about 50° C. and is typically conducted at a temperature in a range of from about 0° C. to about 30° C. The cyclization reaction is typically performed from 1 hour to 24 hours. In one exemplary embodiment, the cyclization step is conducted at a temperature of 25° C.

The final product V could be neutral form (as drawn) or either as a protonated ammonium salt or a deprotonated carboxylate salt. For a protonated salt, the counterion could be a conjugate base of any of the acids listed above. Alternatively, the carboxylic acid could be deprotonated to give inorganic salts (e.g., Na, K, Li, Cs, Ca) or organic salts (e.g., morpholine, $tBuNH_2$, $Cy_2NH$, $Bn_2NH$, TRIS).

The compound of Formula III, or an acidic or basic salt thereof, can be prepared from the starting material (SM)

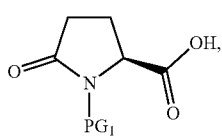

or an acidic or basic salt thereof,
through multiple means including but not limited to those described below.

In one embodiment of the invention, a compound of Formula III, or an acidic or basic salt thereof, is prepared from the starting material (SM), or an acidic or basic salt thereof, by reacting the SM, or an acidic or basic salt thereof, with a sulfur reagent to form a sulfur ylide of Formula II, or an acidic or basic salt thereof, followed by reacting a compound of Formula II, or an acidic or basic salt thereof, with a halide source to form a halooxime of Formula III, or an acidic or basic salt thereof. In certain aspects of this embodiment, the SM is commercially available Boc-pyroglutamic acid (Boc-Pyr-OH).

In one aspect of this embodiment, the process of the invention further comprises preparing a compound of Formula III

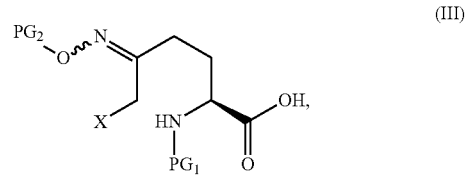

or an acidic or basic salt thereof, wherein X is bromo, iodo or chloro,
by
(A) reacting SM of Formula

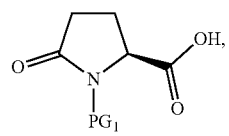

or an acidic or basic salt thereof,
with a sulfur reagent to obtain a sulfur ylide compound of Formula II

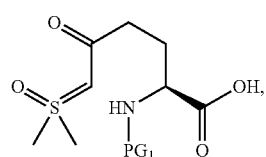

or an acidic or basic salt thereof;
(B) reacting the compound of Formula II, or an acidic or basic salt thereof, with a halide source, acid, and $BnONH_2$ to form a halooxime compound of Formula III, or an acidic or basic salt thereof.

The protecting group $PG_1$ in the SM can be carbamate based ($CO_2R$ e.g., Boc, CBz, Alloc, Teoc, $CO_2Me$, or $CO_2CH_2CH_2TMS$) or amide-based (COR e.g., Acetyl, Benzoyl, or $COCF_3$), wherein R is alkyl or substituted alkyl (e.g., a benzyl). In certain aspects of this embodiment $PG_1$ is preferably Boc.

The reaction in step A is conducted with a sulfur reagent and a suitable non-nucleophilic base stronger than hydroxide. The sulfur reagent can be any molecule with $R_1R_2S^+$ OMe $X^-$ (wherein $R_1$ and $R_2$ are independently methyl or a phenyl group, wherein the phenyl may be substituted; most commonly $Me_3SO$ I, but could be $Me_3SO$ Cl/Br, $Ph_2SOMe$ I/Br/Cl, PhMeSOMe I/Br/Cl, etc. and X is a halogen). Examples of suitable bases include KOtBu, NaOtBu, LiOtBu, potassium t-pentoxide, sodium t-pentoxide, lithium t-pentoxide, NaH, LiHMDS, NaHMDS, KHMDS, and LDA. The sulfur reagent is typically present at 1-3 equivalents. The base is typically present at 2-4 equivalents. In one embodiment, the base is KOtBu.

Step A is conducted in any non-nucleophilic, polar aprotic solvent or any combination thereof. Suitable solvents include DMF, DMSO, DMAc, NMP, DMPU, sulfolane, THF, and 2-MeTHF.

Step A can suitably be conducted at a temperature in a range of from about −50° C. to about 50° C. and is typically conducted at a temperature in a range of from about −30° C. to about 0° C. In one exemplary embodiment, step A is conducted at a temperature of −20 to −10° C.

A halooxime is formed in Step B from the reaction of the SM with a suitable halide source and acid in the presence of a hydroxylamine. A suitable halide source can be any mineral or organic salt where X=Cl, Br, or I (e.g., LiCl, LiX, $R_4N^+X^-$, NaX, KX, $MgX_2$, CuX, $CuX_2$, etc) or mineral acid e.g., HCl, HBr, or HI. The hydroxylamine source can be any $PG_2ONH_2$ or a salt thereof (Note: $PG_2$ must be orthogonal to the nitrogen protecting group on Pyr-OH). Examples of suitable hydroxylamine sources include, but are not limited to, $BnONH_2$, $AllylONH_2$, $TMSOCH_2CH_2ONH_2$, $AcONH_2$, and $BzONH_2$. The halide source is typically employed at 0-10 equivalents (the halide can come from acid or a $PG_2ONH_2$ salt as well). The hydroxylamine source is typically employed at 1-2 equivalents.

The halooxime formation step in Step B is conducted with any acid with a pKa lower than or equal to AcOH. Suitable acids include, but are not limited to, chloroacetic acid, acetic acid, glycolic acid, cyanoacetic acid, $H_3PO_4$, $CF_3CO_2H$, HCl, HBr, $H_2SO_4$, MsOH, TsOH, TfOH. The acid is typically employed at 1-10 equivalents.

Step B is conducted in any solvent that is used in step A. A sulfoxide co-solvent in Step B can be used to improve the reaction impurity profile and yield. Suitable sulfoxide solvents include, but are not limited to DMSO, diethyl sulfoxide, diisopropyl sulfoxide, dipropyl sulfoxide, and dibutyl sulfoxide. In one exemplary embodiment, DMSO is used as a co-solvent.

Step B can suitably be conducted at a temperature in a range of from about −50° C. to about 50° C., for example, over the course of 60 minutes to 48 hours and is typically conducted at a temperature in a range of from about 0° C. to about 40° C., for example, over the course of 60 minutes to 24 hour. In one exemplary embodiment, Step B is conducted at 25° C., for example, over 22 hours.

The halooxime product could be isolated as free acid or inorganic carboxylate salt (e.g., Li, Na, K, Ca, Cs, etc.) or organic carboxylate salt ($Cy_2NH$, morpholine, $tBuNH_2$, TRIS, etc.).

Additional embodiments are directed to each individual step of the processes of the above embodiments alone and to combinations of an individual step with one or more process steps that may be upstream (earlier) or downstream (later).

In the embodiments of processes for preparing the compounds and salts provided above, it is to be understood that each embodiment or instance of an embodiment may be combined with one or more other embodiments and/or instances, to the extent that the combination is consistent with the description of the embodiments and instances. It is further to be understood that the embodiments of compositions and methods provided are understood to include all embodiments of the compounds and/or salts, including such embodiments as result from combinations of embodiments. Further, each of the embodiments described above, variables $PG_1$, $PG_2$, X and reagents, including, e.g., reducing agents, acids, and transition metals are selected independently from each other.

The intermediate diamine 1 is a useful precursor to MK-7655. The compound of Formula I can subsequently be processed as described in International Patent Application No. WO2010/126820 to obtain a beta lactamase inhibitor to prepare 7-oxo-1,6-diazabicyclo[3.2.1]octane-2-carboxamides and esters, in particular, the beta lactamase inhibitor, (2S,5R)-7-oxo-N-piperidin-4-yl-6-(sulfoxy)-1,6-diazabicyclo[3.2.1]octane-2-carboxamide.

In one aspect, the present invention relates to a Process P' for preparing compound 1, or a salt thereof:

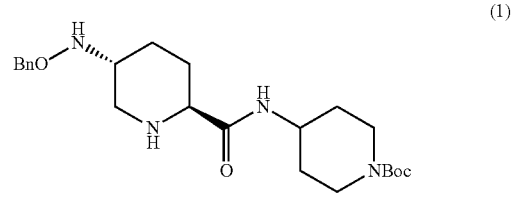 [SMILES: CC(C)(C)OC(=O)N1CCC(NC(=O)[C@@H]2CC[C@@H](NOCc3ccccc3)CN2)CC1]

(1)

which comprises a reduce/couple sequence or a couple/reduce sequence,
wherein:
the reduce/couple sequence comprises
(E1) reducing compound 5:

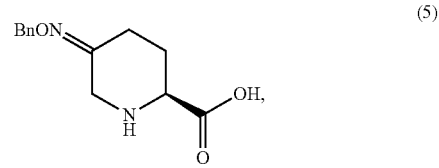

(5)

or an acidic or basic salt thereof,
to obtain compound 6;

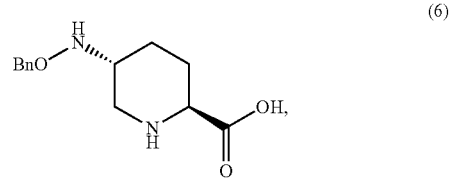 [SMILES: O=C(O)[C@@H]1CC[C@@H](NOCc2ccccc2)CN1]

(6)

or an acidic or basic salt thereof; and
(F1) coupling compound 6, or an acidic or basic salt thereof, with compound 7

(7)

or a salt thereof;
to form compound 1, or a salt thereof;
the couple/reduce sequence comprises
(E2) coupling compound 5:

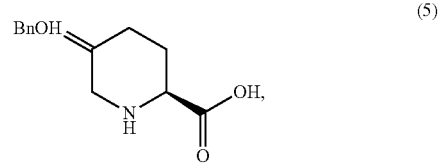

(5)

or an acidic or basic salt thereof,
with compound 7

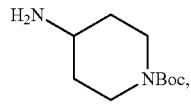
(7)

or a salt thereof,
to obtain compound 8

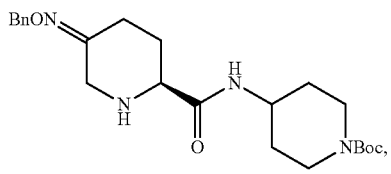
(8)

or a salt thereof; and (F2) reducing compound 8, or a salt thereof, to form compound 1, or a salt thereof. In certain embodiments, PG$_1$ is a first amine protecting group which forms with the amino nitrogen to which it is attached a carbamate, a benzylamine, or a sulfonamide; and PG$_2$ is an oxygen protecting group which in selected embodiments is selected from acetyl (Ac), benzyl (Bn), 4-MeOBn, benzoyl (Bz), and tert-Butyldimethylsilyl ether (TBS).

In one aspect, Process P' comprises the steps described above and further comprises preparing compound 5

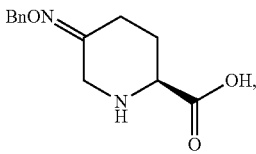
(5)

or an acidic or basic salt thereof,
by step C1 followed by step D1
(C1) cyclizing chlorooxime 3:

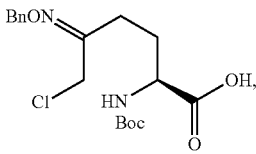
(3)

or a salt thereof,
by addition of a base, such as KOtBu, to obtain compound 4

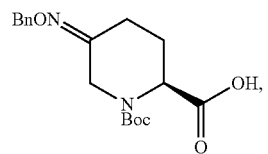
(4)

or a salt thereof, and (D1) deprotecting compound 4, or a salt thereof, to form compound 5, or a salt thereof.

In another aspect, process P' further comprises preparing compound 5

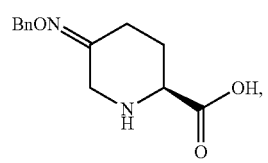
(5)

or an acidic or basic salt thereof,
by step C2 followed by step D2
(C2) deprotecting compound 3, or a salt thereof:

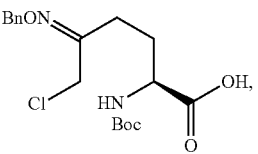
(3)

to obtain compound 9

(9)

or an acidic or basic salt thereof; and (D2) cyclizing compound 9, or an acidic or basic salt thereof, to form compound 5, or an acidic or basic salt thereof.

In certain embodiments, Process P' comprises the steps described above, and further comprises preparation of compound 3 from the starting material (SM) Boc-pyroglutamic acid (Boc-Pyr-OH) by reacting the SM with a sulfur ylide to form compound 2, or a salt thereof, followed by reacting compound 2, or a salt thereof, with an acid, chloride source and BnONH₂ to form compound 3, or a salt thereof.

In one aspect, the process of the invention further comprises preparing compound 3

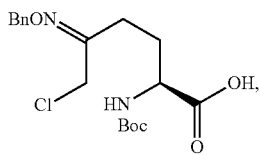

(III)

or a salt thereof,
through Steps A and B below:
(A) reacting Boc-pyroglutamic acid

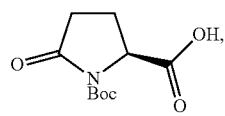 [SMILES: CC(C)(C)OC(=O)N1C(=O)CC[C@H]1C(=O)O]

or a salt thereof,
with a sulfur reagent to obtain a sulfur ylide of compound 2

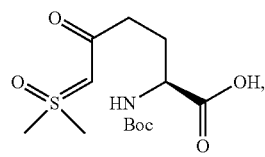

(2)

or a salt thereof;
(B) reacting compound 2, or a salt thereof, with an acid, chloride source, and BnONH₂ to form compound 3, or a salt thereof.

Exemplary Schemes

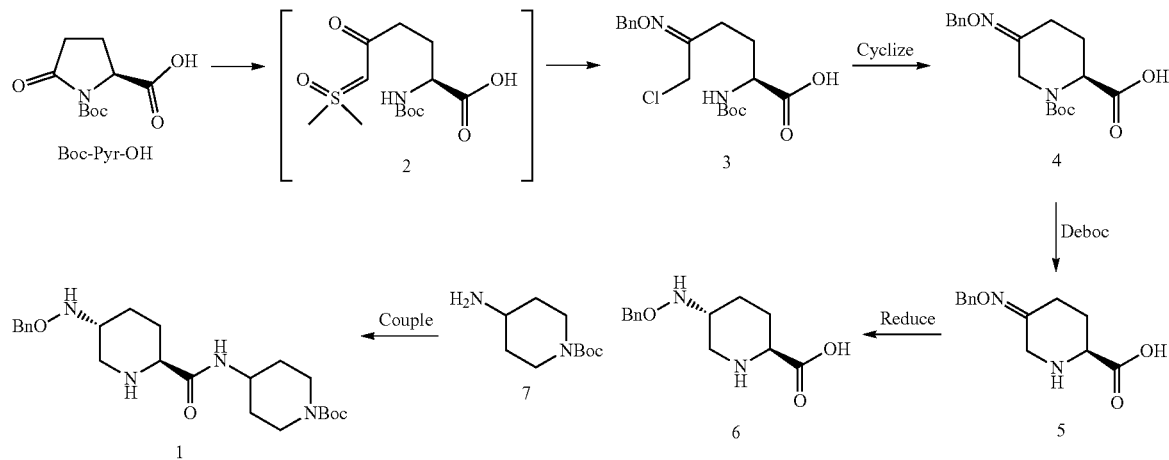

Scheme 1 - Route for preparing the targeted diamine 1

In one variation, the steps Couple and Reduce in Scheme 1 can be reversed from intermediate 5, as shown in Scheme 2 below. This applies the same aspects of coupling the primary amine of 7 in the presence of a secondary amine in 5, then using a highly diastereoselective oxime reduction of 8 to give the desired diamine 1.

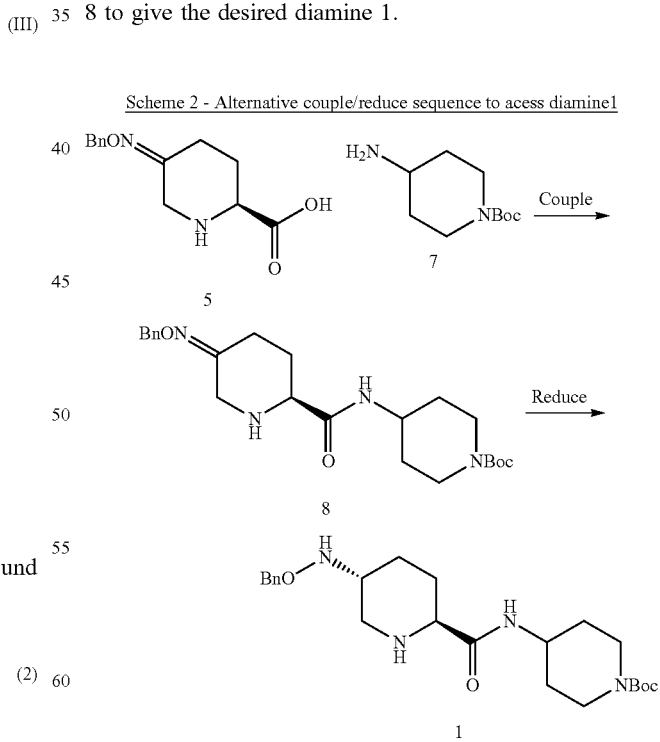

Scheme 2 - Alternative couple/reduce sequence to acess diamine1

A second variation is to reverse the order of steps from 3 to 5 to deboc/cyclize (Scheme 3). This route is generally lower yielding, but proceeds by intermediate 9.

Scheme 3 - Alternative deboc/cyclize route to acess key intermediate 5

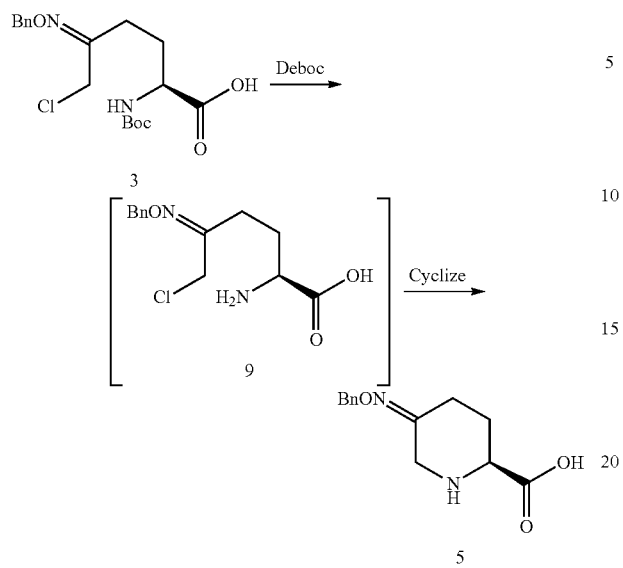

The solvents, agents, catalysts, reaction amounts, reaction temperatures, etc. described above for Steps A to F (including branched steps) in Process P leading to Compound I are applicable to Steps A to F (including branched steps) set forth in Process P' leading to Compound 1, except where express limitations are placed upon one or more of these variables in the various aspects of the invention.

It is to be understood that the solvents, agents, catalysts, reaction amounts, reaction temperatures, etc. described above with respect to Processes P and P', its embodiments and aspects, and individual steps thereof, are intended only to illustrate, not limit, the scope of the process. For example, the solvent employed in any of Steps A to F (including branched steps) unless stated otherwise can be any organic substance which under the reaction conditions employed in the step of interest is in the liquid phase, is chemically inert, and will dissolve, suspend, and/or disperse the reactants and any reagents so as to bring the reactants and reagents into contact and to permit the reaction to proceed. Similar considerations apply to the choice of bases, catalysts, and other reagents employed in the process steps. Furthermore, each of the steps unless stated otherwise can be conducted at any temperature at which the reaction forming the desired product can detectably proceed. The reactants, catalysts and reagents in a given step can be employed in any amounts which result in the formation of at least some of the desired product. Of course, a high conversion (e.g., at least about 60% and preferably higher) of starting materials in combination with a high yield (e.g., at least about 50% and preferably higher) of desired products is typically the objective in each step, and the choice of solvents, agents, catalysts, reaction amounts, temperatures, etc. that can provide relatively good conversions and yields of product are preferred, and the choices that can provide optimal conversions and yields are more preferred. The particular solvents, agents, catalysts, reaction amounts, reaction temperatures, etc. described above with respect to Processes P and P', its embodiments and aspects, and the individual steps thereof can provide good to optimum conversions and yields.

The reaction times for the process steps described above depend upon such factors as (i) the choice and relative proportions of the starting substrate and other reagents, (ii) the choice of solvent, (iii) the choice of reaction temperature, and (iv) the level of conversion desired. The reactions are typically conducted for a time sufficient to achieve 100% or near 100% conversion (e.g., 99.5%, 99.0%, 98.0%, 97.0% or 95%).

The progress of any reaction step set forth herein can be followed by monitoring the disappearance of a reactant and/or the appearance of the desired product using such analytical techniques as TLC, HPLC, IR, NMR or GC.

Unless expressly stated to the contrary, all ranges cited herein are inclusive; i.e., the range includes the values for the upper and lower limits of the range as well as all values in between. For example, a phenyl ring described as optionally substituted with "1 to 3 substituents" is intended to include as aspects thereof, a ring substituted with 1 to 3 substituents, 2 to 3 substituents, 3 substituents, 1 to 2 substituents, 2 substituents, and 1 substituent. As another example, temperature ranges, ranges of equivalents, and the like described herein include the upper and lower limits of the range and any value in the continuum there between.

The present invention further relates to compounds including:

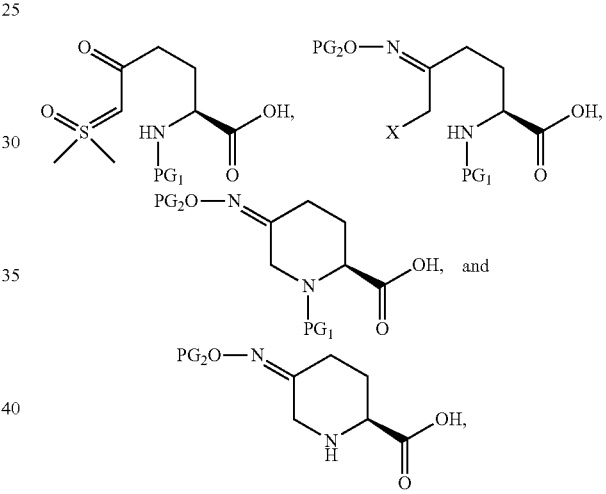

and salts thereof. In certain embodiments, $PG_1$ is Boc, $PG_2$ is benzyl, and X is Cl.

Abbreviations employed herein include the following:

| | |
|---|---|
| Ac | Acetyl |
| Alloc | allyloxycarbonyl |
| BLI | beta-lactamase inhibitor |
| Bn | benzyl |
| Boc | t-butyloxycarbonyl |
| BOP | (Benzotriazol-1-yloxy)tris(dimethylamino)phosphonium hexafluorophosphate |
| BSA | Bis(trimethylsilyl)acetamide |
| Bz | benzoyl |
| Cbz | carbobenzoxy (alternatively, benzyloxycarbonyl) |
| CDI | 1,1'-Carbonyldiimidazole |
| Cy | cyclohexyl |
| DBN | 1,5-Diazabicyclo(4.3.0)non-5-ene |
| DBU | 1,8-Diazabicyclo[5.4.0]undec-7-ene |
| DCC | N,N'-Dicyclohexylcarbodiimide |
| DIC | N,N-Diisopropylcarbodiimide |
| DMAC or DMAc | N,N-dimethylacetamide |
| DMAP | 4-Dimethylaminopyridine |
| DMF | N,N-dimethylformamide |
| DMPU | 1,3-Dimethyl-3,4,5,6-tetrahydro-2(1H)-pyrimidinone |
| DMSO | dimethyl sulfoxide |

-continued

| | |
|---|---|
| DMT | dimethoxytrityl |
| EDC | 1-Ethyl-3-(3-dimethylaminopropyl)carbodiimide |
| EE | ethoxyethyl ethers |
| Et | ethyl |
| EtOAc | ethyl acetate |
| EtOH | ethanol |
| Fmoc | 9-Fluorenylmethoxycarbonyl |
| GC | Gas chromatography |
| HATU | 1-[Bis(dimethylamino)methylene]-1H-1,2,3-triazolo[4,5-b]pyridinium 3-oxid hexafluorophosphate |
| HBTU | 2-(1H-benzotriazol-1-yl)-1,1,3,3-tetramethyluronium hexafluorophosphate |
| HMDS | hexamethyldisilazide |
| HOBt | hydroxybenzotriazole |
| HOBt | 3-hydroxy-1,2,3-benzotriazin-4-one |
| HOPO | 2-pyridinol-1-oxide; 2-hydroxypyridine-N-oxide |
| HOTf | Trifluoromethanesulfonic acid |
| HPLC | high-performance liquid chromatography |
| IPA, i-PrOH | isopropyl alcohol |
| IPAc, i-PrOAc | isopropyl acetate |
| i-Pr₂NH | Diisopropyl amine |
| IR | infrared |
| KOtBu, KOBu-t | Potassium tert-butoxide |
| LDA | lithium diisopropylamide |
| LiOtBu | Lithium tert-butoxide |
| Me | methyl |
| MeCN | acetonitrile |
| Me₃SOI | Trimethylsulfoxonium iodide |
| MeSiOTf | Trimethylsilyl trifluoromethanesulfonate |
| MEM | β-methoxyethoxymethyl ether |
| MeOH | methanol |
| MMT | methoxytrityl |
| Moc | methoxycarbonyl |
| MOM | methoxymethyl ether |
| Ms | Methanesulphonyl |
| MsOH | methanesulfonic acid |
| MTBE | Methyl tert-butyl ether |
| NaOtBu | Sodium tert-butoxide |
| NMP | N-methyl pyrrolidinone |
| NMR | nuclear magnetic resonance |
| OBn | O-benzyl |
| PCy₃ | tricyclohexylphosphine |
| PG | protective (protecting) group |
| Ph | Phenyl |
| PhMe | Phenylmethane, Toluene |
| Piv | pivaloyl |
| PMB | p-methoxybenzyl ether |
| PPh₃ | triphenylphosphine |
| PyBOP | benzotriazol-1-yl-oxytripyrrolidinophosphonium hexafluorophosphate |
| Pyr-OH | Pyroglutamic acid |
| TBDMS | tert-butyldimethylsilyl |
| TBS | tert-Butyldimethylsilyl |
| t-Bu | tert-butyl |
| TCTU | O-(6-Chloro-1-hydrocibenzotriazol-1-yl)-1,1,3,3-tetramethyluronium tetrafluoroborate |
| Teoc | N-[2-(Trimethylsilyl)ethoxycarbonyloxy]succinimide |
| Tf | Trifluoromethanesulfonyl |
| TFA | trifluoroacetic acid |
| THF | tetrahydrofuran |
| THP | tetrahydropyranyl |
| TIPS | triisopropylsilyl |
| TLC | thin layer chromatography |
| TMS | trimethylsilyl |
| TMSBr | Trimethylsilyl bromide |
| TMSI | Trimethylsilyl iodide |
| TOM | tri-isopropylsilyloxymethyl |
| Tr | trityl |
| TRIS | Tris(hydroxymethyl)aminomethane |
| Ts | p-Toluenesulphonyl |
| TsOH | p-Toluenesulfonic acid |

The illustrative examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents allowed under the definitions of Formula I defined above.

The processes of the instant invention are useful in the preparation of compounds of Formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice. The examples are not to be construed as limitations on the scope or spirit of the invention.

EXAMPLES

Example 1A (S)-5-((benzyloxy)imino)-2-((tert-butoxycarbonyl)amino)-6-chlorohexanoic acid (3)

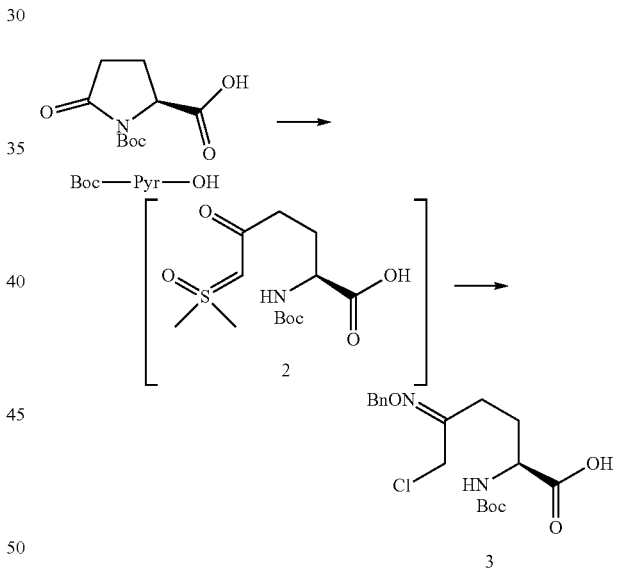

Step A: Preparation of (S)-2-((tert-butoxycarbonyl)amino)-6-(dimethyl(oxo)-λ6-sulfanylidene)-5-oxo-hexanoic acid (2)

A solution of KOtBu (1.0 M in THF, 1.0 equiv) was added to a 0° C. solution of Boc-Pyr-OH (5.0 g, 1.0 equiv)) in DMF (10 mL) over 1 hr. In a separate flask, a solution of KOtBu (1.0 M in THF, 1.1 equiv) was added over 1 hr to a 0° C. slurry of trimethylsufoxonium iodide (1.2 equiv) in DMF (22 mL); the resulting mixture was stirred for 30 min after the end of addition. The thin slurry formed from addition of KOtBu to Boc-Pyr-OH was added over 1 hr to the suspension of sulfur ylide at 0° C. The mixture was stirred for 24 hr while it warmed to ambient temperature, to give a thin slurry of sulfur ylide 2, which was used directly in the next step. M.S. (ESI): 322 (M+H)+

Step B: Preparation of (S)-5-((benzyloxy)imino)-2-((tert-butoxycarbonyl)amino)-6-chlorohexanoic acid (3)

To the slurry of 2 at 0° C. was added a mixture of LiCl (5.0 equiv), chloroacetic acid (3.0 equiv), and O-benzylhydroxylamine hydrochloride (1.0 equiv). The mixture was stirred for 22 hr as it warmed to ambient temperature, then filtered and diluted with IPAc (50 mL). The organic solution was washed with water (3×50 mL), then concentrated to an oil. M.S. (ESI): 385 (M+H)+, 407 (M+Na)+; 1HNMR (DMSO-d$_6$) δ 13.21 (br s, 1H), 7.38-7.18 (m, 5H), 5.09 (br s, 2H), 4.30-4.24 (m, 4H), 3.94-3.83 (m, 1H), 2.51-2.34 (m, 2H), 2.02-1.93 (m, 1H), 1.83-1.72 (m, 1H), 1.72 (s, 9H).

Example 1B

Preparation of (S)-5-((benzyloxy)imino)-2-((tert-butoxycarbonyl)amino)-6-chlorohexanoic acid (3)

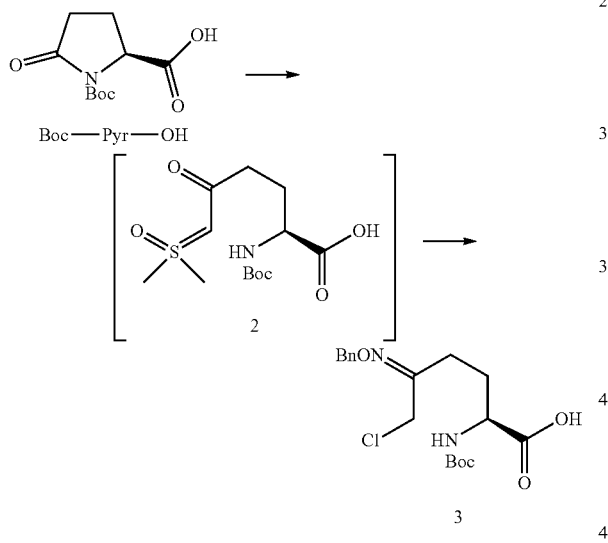

To a mixture of Boc-Pyr-OH (40.0 g) and Me$_3$SOI (49.9 g) in DMF (200 mL) at −20−−10° C. was added a solution of KOBu-t (20 wt % in THF, 231 mL) under a good agitation over 10 hr. Upon completion of addition, the reaction mixture was aged at −20−−10° C. for an additional several hours until completion of the reaction (99% conversion). DMSO (180 mL) and THF (180 mL) were added, while maintaining the internal temperature ≤−5° C. CNCH$_2$CO$_2$H (44.5 g) followed by LiCl (37.0 g) and BnONH$_2$—HCl (27.9 g) was then added in portions, while maintaining the internal temperature ≤0° C. The batch was warmed to 25° C. over 2-3 hr and agitated for an additional 20 hr at 25° C. The reaction mixture was cooled to 15° C. PhMe (240 mL) followed by water (360 mL) was added to quench the reaction, while maintaining the internal temperature ≤25° C. To the separated organic phase was added saturated NaHCO$_3$ aqueous solution (~80 mL) slowly until the pH in the aqueous layer was stable at pH=~5.4. The organic phase was separated and azeotropically dried in vacuum below 35° C. at volume of ~140 mL, which was then directly used for the subsequent step without further purification.

Example 2A (S)-5-((benzyloxy)imino)-1-(tert-butoxycarbonyl)piperidine-2-carboxylic acid (4)

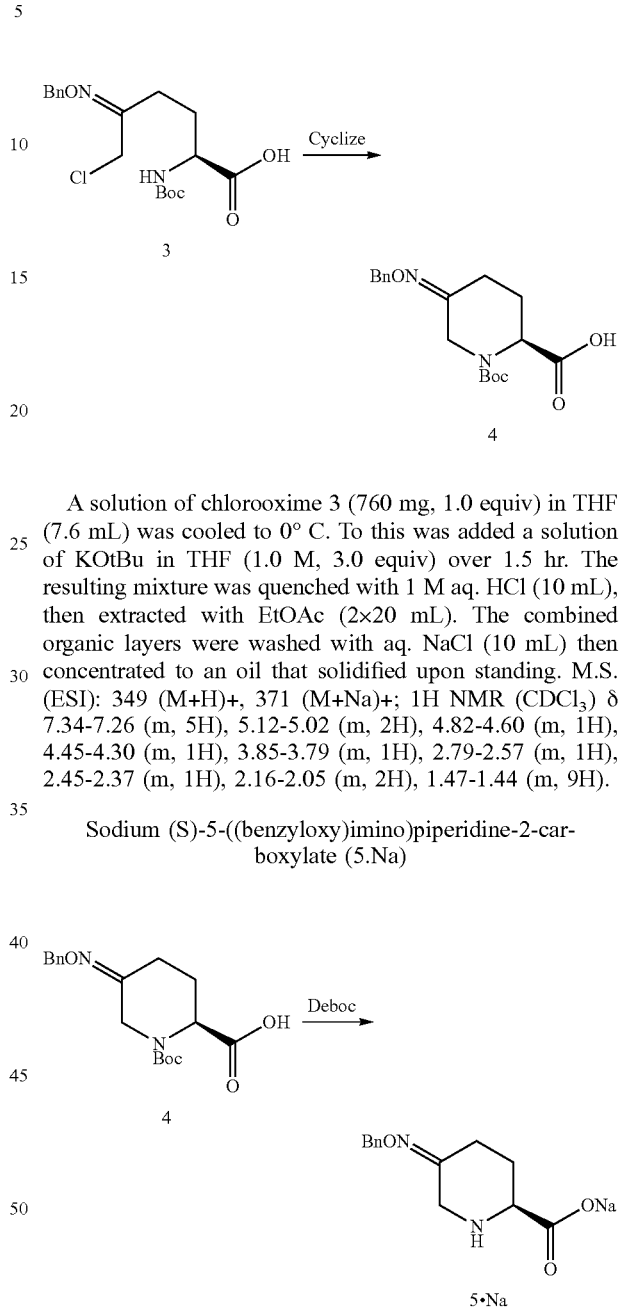

A solution of chlorooxime 3 (760 mg, 1.0 equiv) in THF (7.6 mL) was cooled to 0° C. To this was added a solution of KOtBu in THF (1.0 M, 3.0 equiv) over 1.5 hr. The resulting mixture was quenched with 1 M aq. HCl (10 mL), then extracted with EtOAc (2×20 mL). The combined organic layers were washed with aq. NaCl (10 mL) then concentrated to an oil that solidified upon standing. M.S. (ESI): 349 (M+H)+, 371 (M+Na)+; 1H NMR (CDCl$_3$) δ 7.34-7.26 (m, 5H), 5.12-5.02 (m, 2H), 4.82-4.60 (m, 1H), 4.45-4.30 (m, 1H), 3.85-3.79 (m, 1H), 2.79-2.57 (m, 1H), 2.45-2.37 (m, 1H), 2.16-2.05 (m, 2H), 1.47-1.44 (m, 9H).

Sodium (S)-5-((benzyloxy)imino)piperidine-2-carboxylate (5.Na)

N-Boc piperidine 4 (2.0 g, 1.0 equiv) was dissolved in 2-MeTHF (20 mL) at ambient temperature, then HBF$_4$.OEt$_2$ (1.0 equiv) was added. The mixture was heated to 50° C., and after 30 min additional HBF$_4$.OEt$_2$ (0.25 equiv) was added. After 5 min, the mixture was cooled to 0° C., and a solution of NaOH (3.0 equiv) in MeOH (20 mL) was added over 5 min. The solution was concentrated to a solid, slurried in i-PrOH (15 mL), filtered, and the solid dried under vacuum to give 5.Na. M.S. (ESI): 249 (M-Na+2H)+, 270 (M)+; 1H NMR (CD$_3$OD) δ 7.15-7.09 (m, 5H), 4.85-4.71 (m, 2H), 3.31-3.27 (m, 1H), 3.14-3.07 (m, 3H), 3.03-2.94 (m, 1H), 2.30-1.95 (m, 2H), 1.52-1.41 (m, 1H).

Example 2B (S)-5-((benzyloxy)imino)-1-(tert-butoxycarbonyl)piperidine-2-carboxylic acid (4)

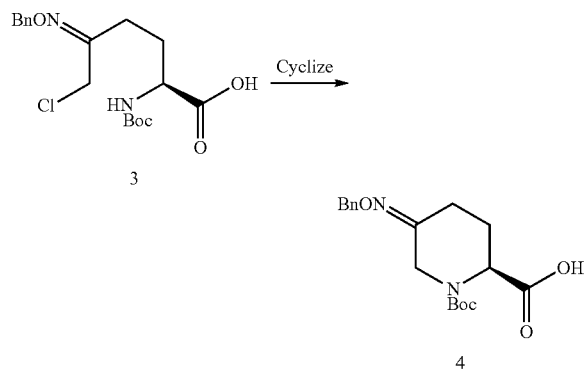

To a solution of chlorooxime 3 (54.0 g assay) in toluene (190 ml) was added DMF (27 mL). The batch was cooled to 0° C. KOtBu (20 wt % in THF, 211 mL) was added dropwise over 3 hr while maintaining the internal temperature below 5° C. After an additional 0.5 hr aging 0-5° C., water (216 mL) was added dropwise, while maintaining the internal temperature below 5° C. MTBE (216 mL) was added to the separated aqueous phase. The batch was then pH adjusted to ~4 with 6 M HCl, while maintaining the internal temperature below 5° C. The separated organic phase was azeotropically dried and solvent switched to MeCN in vacuum below 35° C. to a final volume of ~240 mL, which was directly used for the subsequent step without further purification.

(S)-5-((benzyloxy)imino)piperidine-2-carboxylic acid (5)

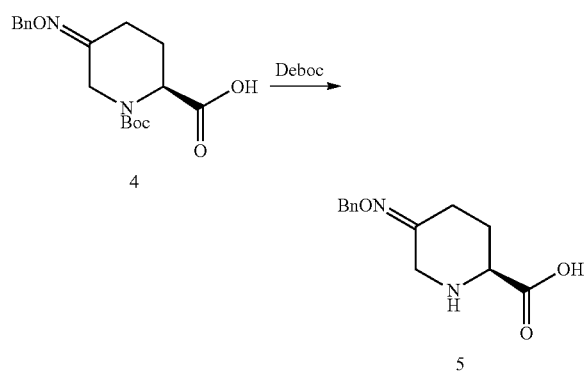

To a mixture of Boc oxime acid 4 (45.0 g assay) in acetonitrile (315 mL) at 15-25° C. was added BSA (17.1 g). The mixture was agitated at ambient temperature for 1 hr, then at 50° C. for 1 hr. The reaction solution was cooled to 0-5° C. TMSBr (35.6 g) was added dropwise at 0-5° C. over 1 hr. After 16-20 hr aging at 25° C., water (10.7 g) was added at 15 to 25° C. slowly. The mixture was aged for an additional 1 hr. A solution of n-Bu$_4$NOAc.AcOH (88.7 g) in MeCN (300 mL) was added dropwise. The batch was seeded after ~50% of the n-Bu$_4$NOAc.AcOH was added. The seeded batch was aged at 15 to 25° C. for 1 hr and then agitated at 50° C. for additional 2 hr. The rest of n-Bu$_4$NOAc acetonitrile solution was added dropwise at 50 to 55° C. over 3 hr. The slurry was agitated at 50 to 55° C. for 4 hr, then cooled to 20° C. and agitated for additional several hours before filtration. The wet cake was displacement washed with 10% water in MeCN (135 mL). The wet cake was slurried in 10% H$_2$O in MeCN (450 mL) at 50-55° C. for 5 hr, then cooled to 20° C. and agitated for additional several hours before filtration. The wet cake was displacement washed with 10% water in MeCN (135 mL). The wet cake was dried in a vacuum oven with N$_2$ sweep at 40-50° C.

An X-ray powder diffraction pattern was generated to characterize the molecular structure of (S)-5-((benzyloxy)imino)piperidine-2-carboxylic acid (5). The pattern was generated on a Panalytical X-pert Pro PW3040 System configured in the Bragg-Brentano configuration and equipped with a Cu radiation source with monochromatization to Kα achieved using a Nickel filter. Data were acquired between 2 and 40° 2θ. Samples were prepared on a shallow cavity zero background silicon holder. The pattern, shown in FIG. 1, exhibited characteristic reflections corresponding to d-spacings as follows.

| No. | Pos. [°2Th.] | d-spacing [Å] |
|---|---|---|
| 1 | 5.0289 | 17.57255 |
| 2 | 6.8981 | 12.81459 |
| 3 | 9.1879 | 9.6254 |
| 4 | 10.0809 | 8.77473 |
| 5 | 10.8548 | 8.15082 |
| 6 | 11.6425 | 7.60106 |
| 7 | 13.8442 | 6.39676 |
| 8 | 14.2005 | 6.23708 |
| 9 | 15.1686 | 5.8411 |
| 10 | 16.2783 | 5.44534 |
| 11 | 17.0044 | 5.2144 |
| 12 | 17.8714 | 4.96334 |
| 13 | 18.6548 | 4.75664 |
| 14 | 18.9013 | 4.69517 |
| 15 | 20.7334 | 4.28424 |
| 16 | 21.7599 | 4.0844 |
| 17 | 22.0582 | 4.02983 |
| 18 | 22.9776 | 3.87063 |
| 19 | 23.3596 | 3.80819 |
| 20 | 24.0052 | 3.70721 |
| 21 | 25.741 | 3.46103 |
| 22 | 26.2103 | 3.40011 |
| 23 | 27.7824 | 3.21118 |
| 24 | 28.6584 | 3.11499 |
| 25 | 30.001 | 2.97858 |
| 26 | 30.6016 | 2.92147 |
| 27 | 32.0627 | 2.79159 |
| 28 | 32.8984 | 2.72257 |
| 29 | 33.943 | 2.64114 |
| 30 | 36.0213 | 2.49338 |
| 31 | 36.775 | 2.44399 |

Example 2C

Sodium (S)-5-((benzyloxy)imino)piperidine-2-carboxylate (5.Na)

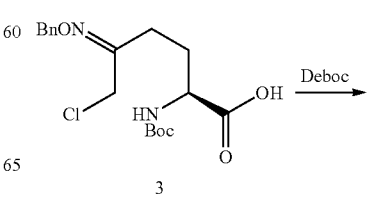

-continued

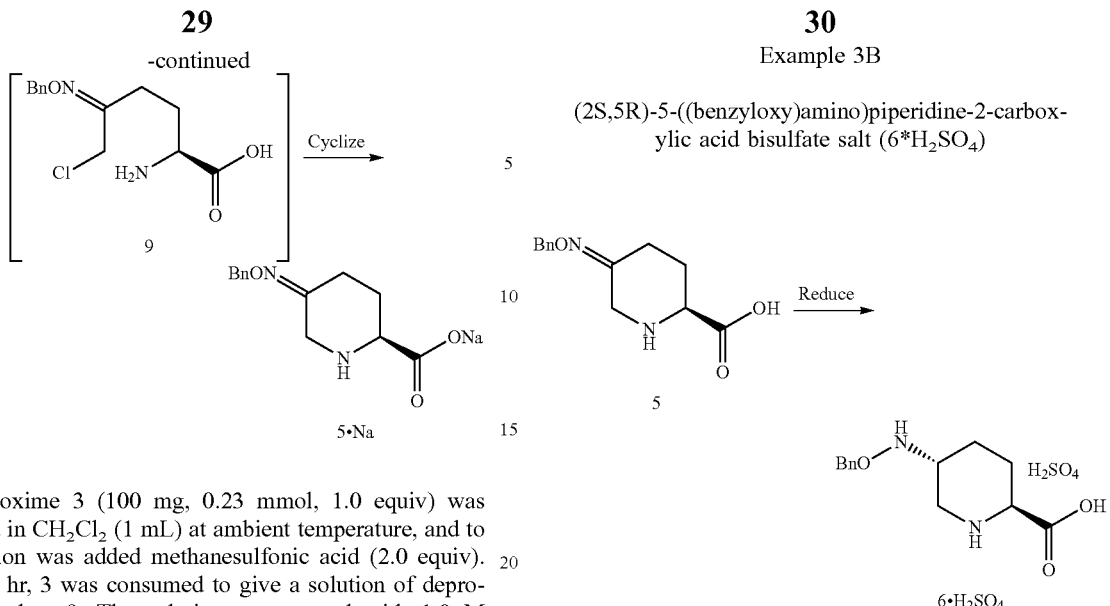

Chlorooxime 3 (100 mg, 0.23 mmol, 1.0 equiv) was dissolved in $CH_2Cl_2$ (1 mL) at ambient temperature, and to the solution was added methanesulfonic acid (2.0 equiv). After 2.5 hr, 3 was consumed to give a solution of deprotected product 9. The solution was treated with 1.0 M aqueous NaOH (3.0 equiv). The resulting slurry was diluted with $CH_3CN$ to make it homogeneous, then concentrated dry to give solid 5.Na.

Example 3A

Sodium (2S,5R)-5-((benzyloxy)amino)piperidine-2-carboxylate (6.Na)

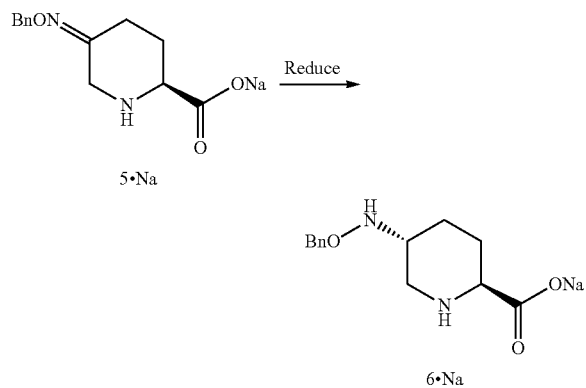

Nitrogen-purged IPA/water (9:1 v/v, 6 mL) was added to a mixture of 5.Na (400 mg, 1.0 equiv), bis(norbornadiene)rhodium(I) tetrafluoroborate (0.05 equiv), and 1,1'-bis(dicyclohexylphosphino)ferrocene (0.05 equiv) in a pressure-rated tube. To this mixture was added $HBF_4 \cdot OEt_2$ (2.0 equiv) and the tube was placed under a hydrogen atmosphere (140 psi). The mixture was stirred under $H_2$ at 50° C. for 18 hr, cooled to ambient temperature, then vented to atmospheric pressure. To the mixture was added NaOH (46 wt % aq. solution, 2.0 equiv) at ambient temperature. The solution was concentrated and the solid dried under vacuum to give 6.Na. M.S. (ESI) 251 (M-Na+2H)+; 1H NMR (CD3OD) δ 7.34-7.32 (m, 5H), 4.66 (s, 2H), 3.00 (dd, J=11.6 Hz, 2.8 Hz, 1H), 2.97-2.89 (m, 1H), 2.36 (dd, J=12.0 Hz, 10.8 Hz, 1H), 2.10 (ddd, J=12.8 Hz, 6.0 Hz, 2.8 Hz), 1.97-1.93 (m, 1H), 1.43 (dq, J=13.2 Hz, 3.6 Hz, 1H), 1.27 (dq, J=12.4 Hz, J=3.6 Hz, 1H)

Example 3B (2S,5R)-5-((benzyloxy)amino)piperidine-2-carboxylic acid bisulfate salt (6*$H_2SO_4$)

To a solution of oxime acid 5 (12.4 g) and $FeCl_3 \cdot 6H_2O$ (21.6 g) in ethanol (100 mL) at −35--3° C. was added a solution of $NaBH_4$ in triglyme (2.06 M, 47.6 mL) dropwise over 15 hr. After completion of the addition, the reaction mixture was agitated at −35--30° C. for an additional several hours. Water (72.5 ml) was added dropwise while maintaining the reaction temperature at ≤10° C. The reaction mixture was agitated at 15-20° C. for 1 hr. Then 10 M $H_2SO_4$ (~4 mL) was added and the batch was seeded with bisulfate salt 6 (350 mg). The seeded batch was aged for 2 hr at 20° C. The rest of the 10 M $H_2SO_4$ (30 mL total) was added over 8 hr at 20-25° C. The slurry was agitated at 20-25° C. until the supernatant concentration of the product was constant before filtration. The wet cake was slurry washed with 0.05 M $H_2SO_4$ (3×37 mL), and dried in a vacuum oven with $N_2$ sweep at 40-50° C.

An X-ray powder diffraction pattern was generated to characterize the molecular structure of (2S,5R)-5-((benzyloxy)amino)piperidine-2-carboxylic acid bisulfate salt (6.$H_2SO_4$) The pattern was generated on a Panalytical X-pert Pro PW3040 System configured in the Bragg-Brentano configuration and equipped with a Cu radiation source with monochromatization to Kα achieved using a Nickel filter. Data were acquired between 2 and 40° 2θ. Samples were prepared on a shallow cavity zero background silicon holder. The pattern, shown in FIG. 2, exhibited characteristic reflections corresponding to d-spacings as follows.

| No. | Pos. [°2Th.] | d-spacing [Å] |
| --- | --- | --- |
| 1 | 7.9877 | 11.06879 |
| 2 | 8.9138 | 9.92085 |
| 3 | 11.1124 | 7.96238 |
| 4 | 14.0046 | 6.32388 |
| 5 | 14.942 | 5.92917 |
| 6 | 15.9999 | 5.53944 |
| 7 | 17.8686 | 4.96413 |
| 8 | 19.0703 | 4.65394 |
| 9 | 20.1948 | 4.39727 |
| 10 | 20.4498 | 4.343 |
| 11 | 20.6927 | 4.29257 |
| 12 | 21.3343 | 4.16491 |
| 13 | 23.3641 | 3.80747 |
| 14 | 24.0962 | 3.69341 |
| 15 | 24.4468 | 3.64123 |

| No. | Pos. [°2Th.] | d-spacing [Å] |
|---|---|---|
| 16 | 25.1506 | 3.54092 |
| 17 | 25.5476 | 3.48678 |
| 18 | 26.0975 | 3.41455 |
| 19 | 26.7215 | 3.33622 |
| 20 | 26.9137 | 3.31282 |
| 21 | 27.1006 | 3.2904 |
| 22 | 27.7595 | 3.21378 |
| 23 | 27.9633 | 3.19082 |
| 24 | 30.321 | 2.94786 |
| 25 | 31.7755 | 2.81617 |
| 26 | 32.3132 | 2.77053 |
| 27 | 33.7489 | 2.65588 |
| 28 | 33.9241 | 2.64257 |
| 29 | 34.3425 | 2.61132 |
| 30 | 35.1227 | 2.55508 |
| 31 | 35.8757 | 2.50316 |
| 32 | 36.3253 | 2.47321 |
| 33 | 36.8181 | 2.44123 |
| 34 | 37.1786 | 2.41838 |
| 35 | 37.5909 | 2.39082 |
| 36 | 37.7189 | 2.38497 |
| 37 | 38.6995 | 2.32677 |
| 38 | 39.4294 | 2.28537 |

Example 4 tert-butyl (S)-4-(5-((benzyloxy)imino)piperidine-2-carboxamido)piperidine-1-carboxylate (8)

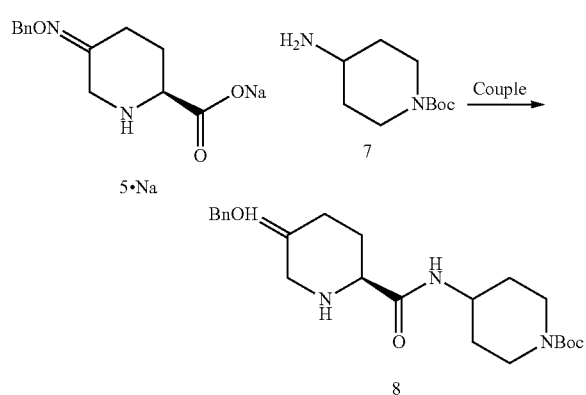

To a slurry of 5·Na (336 mg, 1.0 equiv), tert-butyl 4-aminopiperidine-1-carboxylate (7, 1.1 equiv), EDC.HCl (1.4 equiv), and HOPO (1.0 equiv) in CH₃CN (7.4 mL) was added conc. HCl (2.0 equiv) at ambient temperature. The mixture was stirred at ambient temperature for 2 hr, then diluted with water (3 mL) to give 8. M.S. (ESI): 431 (M+H)+; ¹H NMR (CDCl₃) δ 7.34-7.28 (m, 5H), 5.12-5.08 (m, 2H), 4.15-3.89 (m, 4H), 3.67-3.49 (m, 2H), 3.04-2.85 (m, 3H), 2.40-2.19 (m, 3H), 1.93-1.85 (m, 3H), 1.48 (s, 9H), 1.47-1.34 (m, 2H)

Example 5A tert-butyl 4-((2 S,5R)-5-((benzyloxy)amino)piperidine-2-carboxamido)piperidine-1-carboxylate

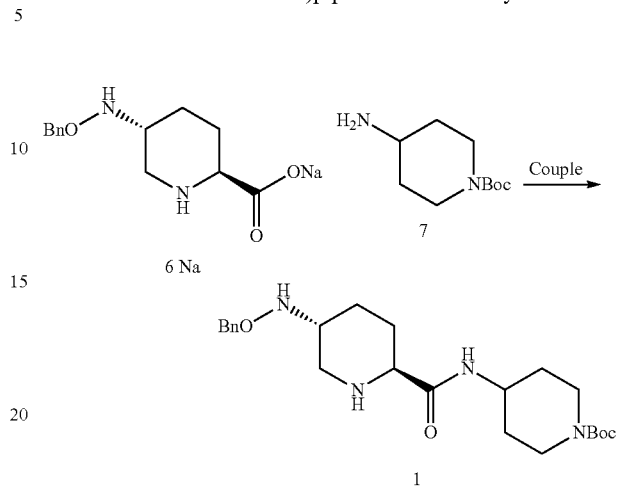

A mixture of carboxylate 6 Na (2.2 g, 1.0 equiv), tert-butyl 4-aminopiperidine-1-carboxylate (7, 1.1 equiv), EDC.HCl (1.4 equiv), and HOPO (1.0 equiv) in DMF (22 mL) was treated with conc. HCl (2.0 equiv) at ambient temperature. After 4 hr, a further charge of 7 (0.2 equiv) and EDC.HCl (0.2 equiv) was made to the mixture. After 17 hr, the mixture was diluted with water (10 mL), KOH solution (15% in water, 15 mL), then extracted with EtOAc (3×25 mL). The combined organic extracts were washed with brine (10 mL), then concentrated to give 1. M.S. (ESI): 433 (M+H)+; ¹H NMR data matched those previously reported [*Org. Lett.* 2014, 16, 174].

Example 5B tert-butyl 4-((2 S,5R)-5-((benzyloxy)amino)piperidine-2-carboxamido)piperidine-1-carboxylate pTSA salt (1)

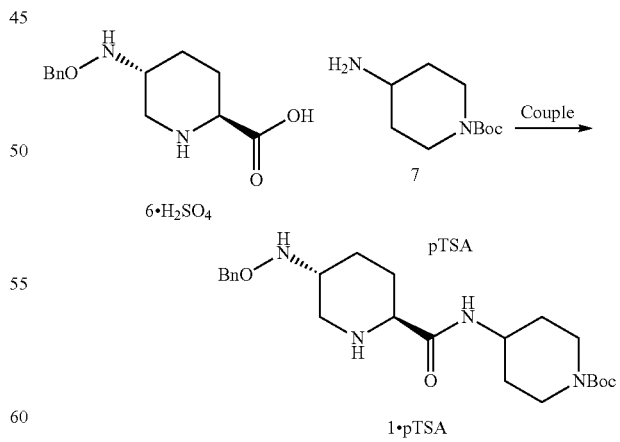

To a solution of CF₃CO₂Na (6.88 g) in N-Methyl-2-pyrrolidinone (100 mL) was added (2S,5R)-5-((benzyloxy)amino)piperidine-2-carboxylic acid sulfuric acid salt (7, 10.0 g). The batch was agitated at 50° C. for 1 hr to form a hazy solution. The batch was then cooled to ambient temperature. ~55% of the resulting solution was added to a mixture of amine 7 (6.72 g) in toluene (30 mL) at ambient temperature. HOPO (2.81 g) followed by 2,6-lutidine (5.89 ml) was added. The reaction mixture was cooled to 0° C. EDC-HCl (7.27 g) was then added. The remaining solution of compound 6 H₂SO₄ salt and CF₃CO₂Na in NMP was added at 0° C. over 15 hr. The reaction mixture was then stirred at 0 hr for an additional 1 day. The reaction mixture was added dropwise to a cold solution of sat'd. aq. NH₄OH (100 mL) and toluene (50 mL), while maintaining the internal temperature below 0° C. The quenched batch was agitated at 0° C. overnight. The aqueous layer was separated and extracted with toluene (2×50 mL). The combined organic phase was washed with 10% aqueous LiCl three times (80 mL, 50 mL and 30 mL). The organic phase was azeotropically concentrated at a volume of ~40 mL, while maintaining the internal temperature below 35° C. MeCN (10 mL) was added and the batch was cooled to 25° C. A solution of TsOH (5.8 g) in acetonitrile (15 mL) and water (1.5 mL) was added dropwise. The batch was seeded after about 30% of the above TsOH solution was added. The seeded batch was agitated for 1 hr. The rest of the TsOH solution was added over 2 hr. The slurry was cooled to 0° C. and agitated for additional 2 hr before filtration. The wet cake was washed with a cold (0° C.) mixture of toluene:MeCN (75:25, 3×20 mL), and dried in a vacuum oven with N₂ sweep at 40° C.

Example 5C tert-butyl 4-((2S,5R)-5-((benzyloxy)amino)piperidine-2-carboxamido)piperidine-1-carboxylate

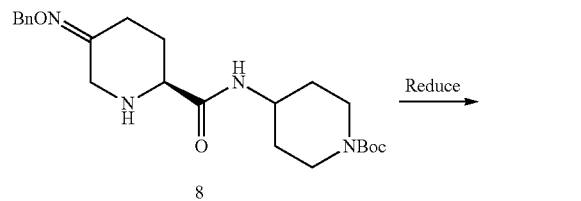

A mixture of 8 (250 mg, 1.0 equiv), bis(norbornadiene)rhodium(I) tetrafluoroborate (0.02 equiv), and 1,1'-bis(dicyclohexylphosphino)ferrocene (0.02 equiv) was suspended in nitrogen-purged EtOH (3 mL) at ambient temperature. To the mixture was added HBF₄·OEt₂ (1.0 equiv), and this was placed under a hydrogen atmosphere (120 psi). The mixture was stirred under H₂ at 50° C. for 22 hr, cooled to ambient temperature, then concentrated to a solid to give 1. M.S. (ESI): 433 (M+H)⁺; ¹H NMR data matched those previously reported [*Org. Lett.* 2014, 16, 174].

Example 6

(S)-5-((benzyloxy)imino)piperidine-2-carboxylate (5)

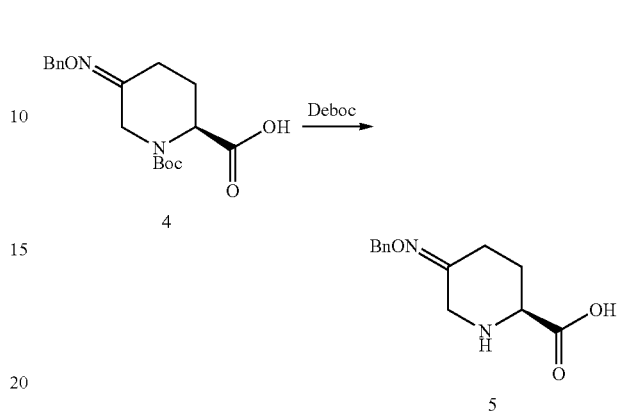

An alternative route to compound 5 from compound 4 was developed.

To a solution of Boc oxime acid 4 (3 g) in CH₂Cl₂/toluene (1:1 to 3:7 mixture, 30 mL) was added methanesulfonic acid (0.91 g) and stirred at room temperature until >98% conversion. The resulting slurry was filtered and washed with toluene and vacuum dried to afford compound 5 as the mesylate salt. ¹H NMR (MeOH-d₄) (2 oxime geometric isomers) δ 7.38-7.27 (m, 5H), 5.15-5.08 (m, 2H), 4.64 & 3.73 (d, J=15.2 Hz, 1H), 4.28-4.21 (m, 1H), 3.86 (dd, J=31.8, 14.3 Hz, 1H), 3.33 & 2.36 (m, 1H), 2.70 (s, 3H), 2.66-2.53 (m, 1H), 2.49-2.40 (m, 1H), 1.96 & 1.87 (m, 1H). ¹³C NMR (MeOH-d₄) (2 oxime geometric isomers) δ 170.50 & 170.44, 150.31 & 149.02, 138.85 & 138.59 (aromatic), 129.5 & 129.43 & 129.42 & 129.34 & 129.12 & 129.03 (aromatic), 77.51 & 77.41, 57.41 & 56.92, 46.64 & 39.88, 39.47, 27.98 & 25.43, 26.23 & 22.51.

Example 7

(2S,5R)-5-((benzyloxy)amino)piperidine-2-carboxylate (6)

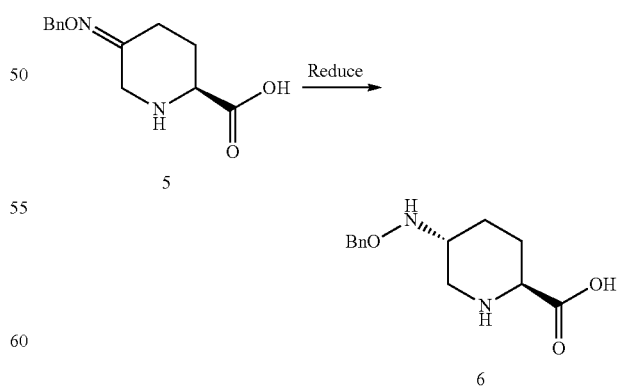

An alternative method to obtain compound 6 from compound 5 was developed.

To a mixture of mesylate salt of 5 (0.2 g) in EtOAc (2.6 mL) or acetonitrile (2.6 mL) was added 96% H₂SO₄ (0.19 mL). The solution was cooled to −50° C. (or −15° C.). A slurry of NaBH₄ (0.073 g) and 96% formic acid (0.23 mL) in EtOAc (2.6 mL) or acetonitrile (2.6 mL), which has been stirred for 1 hr at rt, was slowly added at <−40° C. (or <−10° C.). The mixture was allowed to slowly warm to rt overnight. To the resulting slurry was added H₂O (4.5 mL) and stirred at rt overnight. The slurry was filtered and washed with EtOAc (2 mL) or acetonitrile (2 mL) and H₂O (0.7 mL). The wet cake was vacuum dried under N₂ to afford product 6 as the bisulfate salt. ¹H NMR (DMSO-d₆+ traces of MeOH-d₄) δ 7.40-7.25 (m, 5H), 4.58 (s, 2H), 3.93 (d, J=11.7 Hz, 1H), 3.38 (d, J=11.9 Hz, 1H), 3.11 (m, 1H), 2.70 (t, J=11.9 Hz, 1H), 2.18 (dd, J=14.2, 3.5 Hz, 1H), 1.87 (d, J=12.3 Hz, 1H), 1.66 (dd, J=26.3, 13.4 Hz, 1H), 1.42 (dd, J=25.1, 12.5 Hz, 1H). ¹³C NMR (DMSO-d₆+ traces of MeOH-d₄) δ 170.5, 138.0, 127.0 (2C), 127.8, 76.0, 55.9, 53.2, 45.6, 25.4, 24.4. MS (ES+) m/z=251.21.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a compound of Formula I, or a salt thereof:

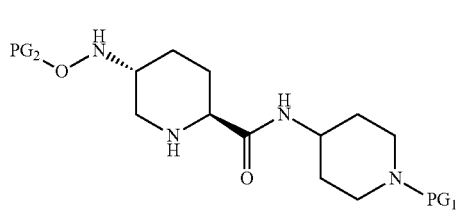

(I)

which comprises a reduce/couple sequence or a couple/reduce sequence,
wherein:
the reduce/couple sequence comprises
(E1) reducing a compound of Formula V

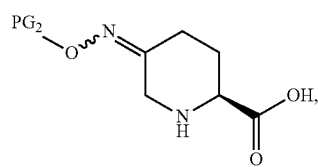

(V)

or an acidic or basic salt thereof,
to obtain a compound of Formula VI

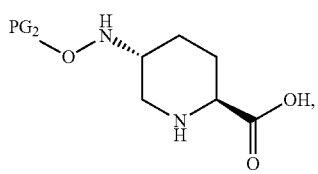

(VI)

or an acidic or basic salt thereof; and
(F1) coupling the compound of Formula VI, or an acidic or basic salt thereof, with a compound of formula VII

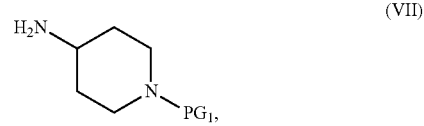

(VII)

or a salt thereof;
to form the compound of Formula I, or a salt thereof;
the couple/reduce sequence comprises
(E2) coupling a compound of Formula V:

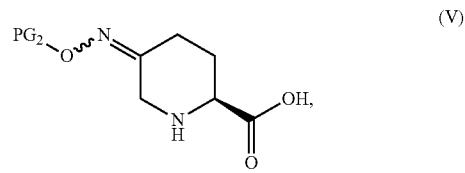

(V)

or an acidic or basic salt thereof,
with a compound of Formula VII

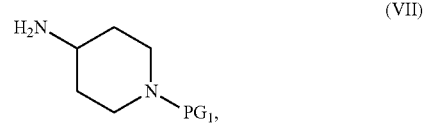

(VII)

or a salt thereof,
to obtain a compound of Formula VIII

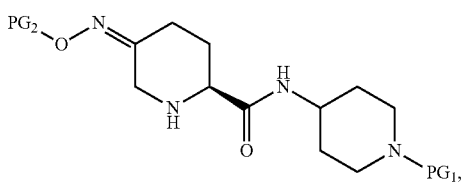

(VIII)

or a salt thereof; and
(F2) reducing the compound of Formula VIII, or a salt there, to form the compound of Formula I, or a salt thereof;
PG₁ is an amine protecting group which forms with the amino nitrogen to which it is attached a carbamate, a benzylamine, or a sulfonamide; and
PG₂ is an oxygen protecting group selected from acetyl (Ac), benzyl (Bn), 4-MeOBn, benzoyl (Bz), and tert-Butyldimethylsilyl ether (TBS).

2. The process according to claim 1, wherein the reduction step in step E1 or F2 is conducted with a mono or bidentate phosphine in the presence of 1) a transition metal in a polar solvent or 2) a borohydride reagent and a protic or Lewis acid in a suitable solvent.

3. The process according to claim 2, wherein the phosphine is bis(dicyclohexylphosphino)-ferrocene, triphenylphosphine, tricyclohexylphosphine, or 1,1'-Bis(diphenylphosphino)ferrocene.

4. The process according to claim 2, wherein the reaction is conducted in the presence of a transition metal in a polar solvent and the transition metal is Rh(I), Ru, Pd, Ni, or Cu.

5. The process according to claim 4, wherein the transition metal is Rh(I) in the form of bis(norbornadiene)rhodium(I) tetrafluoroborate.

6. The process according to claim 2, wherein the reaction is conducted in the presence of a borohydride reagent, and an acid in a suitable solvent including water, the borohydride reagent is $NaBH_4$, the suitable solvent is ethanol or an ethanol/triglyme mixture, the acid is a Lewis acid selected from a Fe(III) halide or a Fe(III) salt, wherein the water can be in the form of a hydrate salt of Fe(III) halide or Fe(III) salt.

7. The process according to claim 2, wherein the reaction is conducted in the presence of a borohydride reagent and a protic acid in a polar solvent, the borohydride reagent is a carboxylic acid modified $NaBH_4$, the polar solvent is acetonitrile or ethyl acetate, and the protic acid is $H_2SO_4$.

8. The process according to claim 1, wherein the coupling step in step E2 or F1 is conducted in the presence of a coupling reagent in a non-nucleophilic solvent system and optionally a peptide coupling additive and optionally an acid or a base additive.

9. The process according to claim 8, wherein the coupling reagent is 1-Ethyl-3-(3-dimethylaminopropyl)carbodiimide HCl (EDC.HCl).

10. The process of claim 8 wherein the non-nucleophilic solvent system comprises one or more of $CH_3CN$, NMP, toluene or DMF.

11. The process of claim 8 wherein the peptide coupling additive is HOPO.

12. The process of claim 8 wherein the additive is $CF_3CO_2Na$.

13. The process of claim 8 wherein the base additive is lutidine.

14. The process of any one of claims 1 to 13, wherein $PG_1$ is Boc and $PG_2$ is benzyl.

15. The process according to claim 1, which further comprises preparing a compound of Formula V

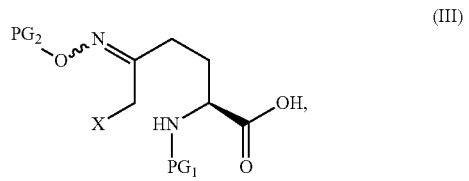

or an acidic or basic salt thereof,
by Step C1 followed by Step D1
(C1) cyclizing a halooxime of Formula III:

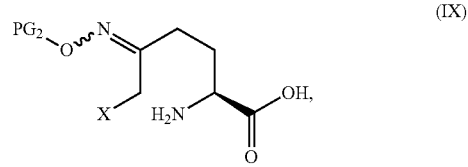

or an acidic or basic salt thereof, wherein X is bromo or chloro, by addition of a base in a solvent to obtain a compound of Formula IV

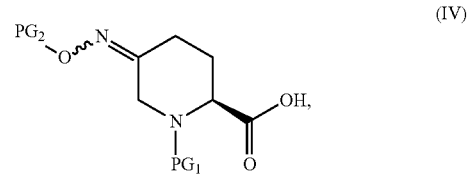

or an acidic or basic salt thereof; and
(D1) deprotecting the compound of Formula IV, or a salt thereof, to form a compound of Formula V, or an acidic or basic salt thereof.

16. The process of claim 15, wherein the base is KOtBu.

17. The process of claim 15, wherein the solvent is THF, DMF, or toluene.

18. The process of claim 15, wherein the deprotection step is conducted with a protic acid, Lewis acid or nucleophilic base in a solvent.

19. The process of claim 18, wherein the deprotection step is conducted with a Lewis acid, and optionally BSA, in a solvent, wherein the Lewis acid is TMSBr or TMSI.

20. The process according to claim 1, which further comprises preparing a compound of Formula V

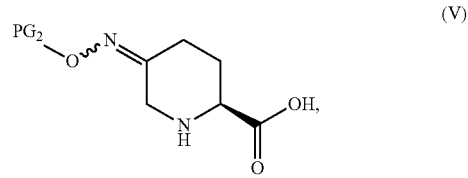

or an acidic or basic salt thereof,
by Step C2 followed by Step D2
(C2) deprotecting a compound of Formula III in a strong acid in a non-nucleophilic solvent:

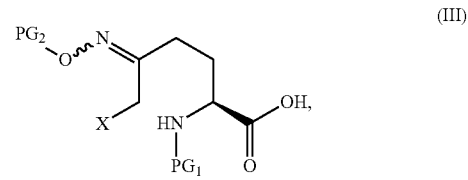

or a salt thereof
to obtain a compound of Formula IX

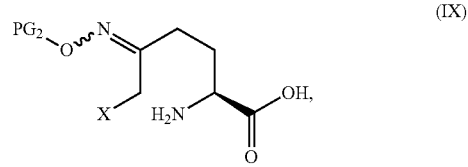

or an acidic or basic salt thereof; and
(D2) cyclizing the compound of Formula IX, or an acidic or basic salt thereof, with a base to form a compound of Formula V, or an acidic or basic salt thereof;

wherein X is bromo or chloro.

21. The process of claim 20, wherein the acid is MsOH.

22. The process of claim 20, wherein the solvent is CH$_2$Cl$_2$.

23. The process of claim 20, wherein the base is NaOH.

24. The process of claim 20, wherein the solvent is CH$_2$Cl$_2$/H$_2$O.

25. The process according to claim 1 or 2, which further comprises preparing a compound of Formula III

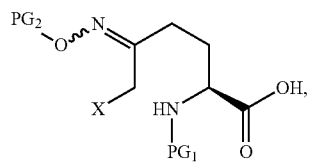

(III)

or a salt thereof, wherein X is bromo or chloro, through Steps A and B below:

(A) reacting SM of Formula

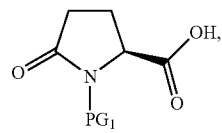

or a salt thereof, with a sulfur reagent to obtain a sulfur ylide compound of Formula II

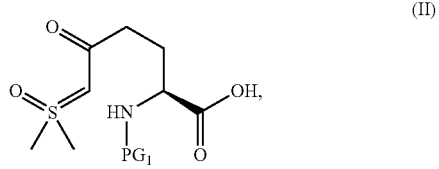

(II)

or a salt thereof;

(B) reacting the compound of Formula II, or a salt thereof, with a halide source to form a halooxime compound of Formula III, or a salt thereof.

26. The process of claim 22, wherein the sulfur reagent is Me$_3$SOI and the non-nucleophilic base is KOtBu.

27. The process of claim 22, wherein the solvent in step (A) is a mixture of THF and DMF.

28. The process of claim 22, wherein the halide source is LiCl and the acid is chloroacetic acid or cyanoacetic acid.

29. The process of claim 22, wherein the solvent in step (B) is a mixture of THF, DMF and DMSO.

* * * * *